(12) United States Patent
Makino

(10) Patent No.: US 11,436,728 B2
(45) Date of Patent: Sep. 6, 2022

(54) ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

(*) Notice: Subject to any disclaimer, the term of this patent is extended or adjusted under 35 U.S.C. 154(b) by 177 days.

(21) Appl. No.: 16/963,405

(22) PCT Filed: Feb. 6, 2019

(86) PCT No.: PCT/JP2019/004147
§ 371 (c)(1),
(2) Date: Jul. 20, 2020

(87) PCT Pub. No.: WO2019/159770
PCT Pub. Date: Aug. 22, 2019

(65) Prior Publication Data
US 2021/0133974 A1    May 6, 2021

(30) Foreign Application Priority Data

Feb. 13, 2018  (JP) .............................. JP2018-023111
Oct. 22, 2018  (WO) .................. PCT/JP2018/039235

(51) Int. Cl.
*G06K 9/00*      (2022.01)
*G06T 7/00*      (2017.01)
(Continued)

(52) U.S. Cl.
CPC .............. *G06T 7/0014* (2013.01); *G06T 7/11* (2017.01); *G06T 7/90* (2017.01); *A61B 1/00006* (2013.01);
(Continued)

(58) Field of Classification Search
CPC . G06T 7/0014; G06T 7/11; G06T 7/90; G06T 2207/10024; G06T 2207/10068;
(Continued)

(56) References Cited

U.S. PATENT DOCUMENTS

2014/0320620 A1* 10/2014 Ikemoto ............. A61B 1/00009
                                                        348/71
2016/0007829 A1    1/2016 Chun
                     (Continued)

FOREIGN PATENT DOCUMENTS

JP    2005-192880    7/2005
JP    2006-218138    8/2006
                (Continued)

OTHER PUBLICATIONS

Official Communication issued in International Bureau of WIPO Patent Application No. PCT/JP2019/004147, dated Apr. 16, 2019.

*Primary Examiner* — Andrew M Moyer
(74) *Attorney, Agent, or Firm* — Greenblum & Bernstein, P.L.C.

(57) ABSTRACT

An endoscope system includes an image processing unit obtaining a severity of a lesion of a biological tissue in which a degree of lesion is digitized, from an image of the biological tissue that is obtained by imaging the biological tissue in a body cavity. The image processing unit includes a feature amount calculation unit calculating a plurality of pixel evaluation values corresponding to a plurality of features of an appearance, which are capable of discriminating each of the plurality of features of the appearance from a feature of a normal portion of the biological tissue by a shape and indicate each degree of plurality of features relevant to the color component indicated by the lesion portion or the color component and the shape, a representative value calculation unit calculating a representative evaluation value corresponding to each of the plurality of features of the imaged biological tissue.

14 Claims, 9 Drawing Sheets

(51) Int. Cl.
*G06T 7/11* (2017.01)
*G06T 7/90* (2017.01)
*A61B 1/00* (2006.01)
*A61B 1/05* (2006.01)
*A61B 1/06* (2006.01)
*A61B 1/07* (2006.01)

(52) U.S. Cl.
CPC ............ *A61B 1/00096* (2013.01); *A61B 1/05* (2013.01); *A61B 1/0669* (2013.01); *A61B 1/07* (2013.01); *G06T 2207/10024* (2013.01); *G06T 2207/10068* (2013.01); *G06T 2207/30096* (2013.01); *G06T 2207/30101* (2013.01)

(58) Field of Classification Search
CPC . G06T 2207/30096; G06T 2207/30101; G06T 2207/30028; A61B 1/00006; A61B 1/00096; A61B 1/05; A61B 1/0669; A61B 1/07; A61B 1/000094; A61B 1/045
See application file for complete search history.

(56) References Cited

U.S. PATENT DOCUMENTS

| | | |
|---|---|---|
| 2017/0280971 A1 | 10/2017 | Makino |
| 2018/0153384 A1 | 6/2018 | Ikemoto et al. |
| 2018/0184882 A1 | 7/2018 | Makino |
| 2018/0279866 A1 | 10/2018 | Makino |
| 2019/0343369 A1 | 11/2019 | Makino et al. |

FOREIGN PATENT DOCUMENTS

| | | | |
|---|---|---|---|
| JP | 2009-247463 | 10/2009 | |
| JP | 2016-158682 | 9/2016 | |
| WO | 2014/156938 | 10/2014 | |
| WO | WO-2016136698 A1 * | 9/2016 | ......... A61B 1/00009 |
| WO | 2016/208748 | 12/2016 | |
| WO | 2017/026539 | 2/2017 | |
| WO | 2017/057680 | 4/2017 | |
| WO | 2018/043551 | 3/2018 | |

* cited by examiner

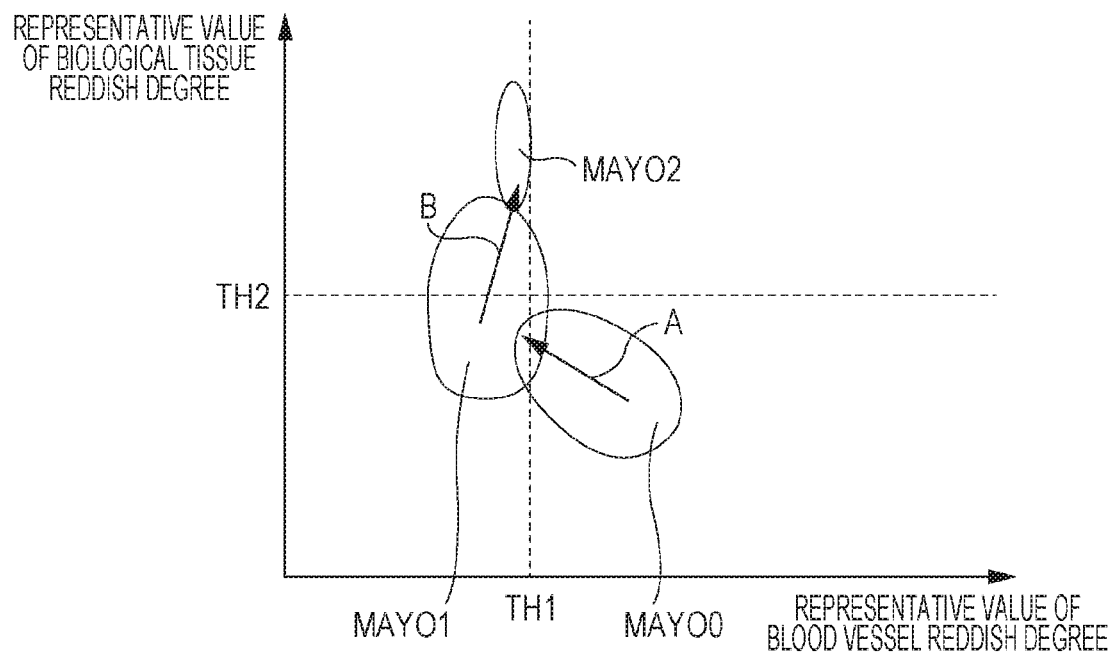

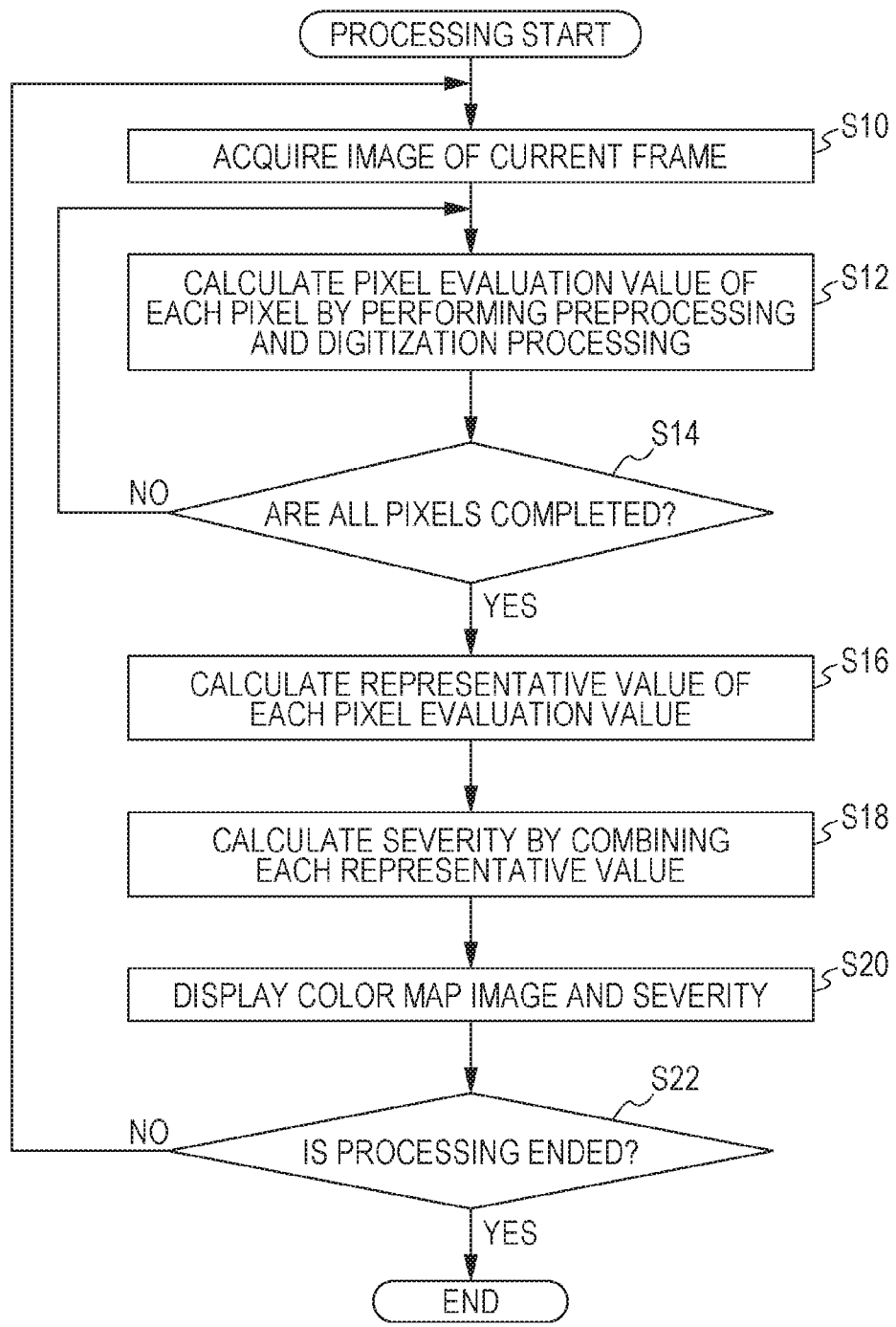

ENDOSCOPE SYSTEM

TECHNICAL FIELD

The present invention relates to an endoscope system performing image processing with respect to an image of a biological tissue in a body cavity.

BACKGROUND ART

A lesion portion in a biological tissue has various levels of severity from an inflammation in which a mucosal layer of the biological tissue becomes thin and rough, and exhibits a red color to an ulcer in which a partial loss occurs in the mucosal layer and a lower layer thereof. For example, an ulcer site of a lesion of an ulcerative colitis (UC) that includes tongue fur or mucopus exhibits a white color, and an inflamed site that includes edema or easy bleeding properties exhibits a red color. Such a lesion portion can be observed by being imaged with an endoscope system.

However, in order to enable an operator to identify a normal site and a lesion portion by a color difference in an image of an endoscope, it is necessary to receive long-term training under the guidance of a skilled person. In addition, it is not easy for even a skilled operator to identify the lesion portion from a slight color difference, and a cautious operation is required. Therefore, it is preferable that the endoscope system provides evaluation results in which the degree of lesion in the lesion portion is objectively digitized.

In response, an endoscope system is known in which a stable evaluation value can be calculated by suppressing a variation in an evaluation value of an inflamed site due to the brightness of an image, and a processing load for calculating the evaluation value can be suppressed (Patent Literature 1).

CITATION LIST

Patent Literature

Patent Literature 1: WO 2017/057680 A

SUMMARY OF INVENTION

Technical Problem

The endoscope system described above includes a light source device applying illumination light toward an object, an image acquisition unit acquiring a color image including at least three or more color components by receiving and imaging reflection light from the object with an image sensor, and an evaluation unit obtaining an evaluation result relevant to a target illness of each pixel on the basis of an angle between a line segment connecting a predetermined reference point set in a color plane that is defined by at least two color components of at least three or more color components and a pixel corresponding point in a color plane of each of the pixels configuring the color image that is acquired by the image acquisition unit, and a reference axis having a correlation with the target illness. The reference axis is set to pass through the predetermined reference point. The reference axis is at least one of an axis having a correlation with the target illness in which the degree of inflammation in the color plane is less than or equal to a predetermined value and an axis having a correlation with the target illness in which the degree of in lamination is greater than or equal to the predetermined value.

According to such a configuration, a stable inflammation evaluation value can be calculated by suppressing a variation in an inflammation evaluation value due to the brightness of the image, and a processing load for calculating the inflammation evaluation value can be suppressed.

However, a lesion portion that can be evaluated by the endoscope system is an inflamed site in which a mucosal layer of a biological tissue becomes thin and rough, and exhibits a red color, and the degree of inflammation of the inflamed site is evaluated as a color component, and thus, may not sufficiently correspond to a subjective evaluation result of a medical doctor, including an inflammation to an ulcer, or a histological evaluation result. That is, the endoscope system is not capable of evaluating a severity indicating the degree of lesion in the lesion portion including an ulcer in which a partial loss occurs in the mucosal layer and a lower layer thereof.

Therefore, an object of the present invention is to provide an endoscope system that is capable of accurately evaluating the degree of lesion in a lesion portion of a biological tissue.

Solution to Problem

One embodiment of the present invention is an endoscope system. The endoscope system, includes:

an electronic endoscope configured to image a biological tissue in a body cavity;

a processor including an image processing unit configured to obtain a severity of a lesion of the biological tissue in which a degree of lesion is represented as one value by using at least information of a color component of an image of a lesion portion of the biological tissue, from the image that is obtained by the electronic endoscope; and a monitor configured to display information of the severity. The image processing unit includes a feature amount calculation unit configured to calculate a plurality of pixel evaluation values corresponding to a plurality of features of an appearance, including at least a first feature and a second feature of an appearance appearing in the lesion portion, which are capable of discriminating each of the plurality of features of the appearance from a feature of a normal portion of the biological tissue by a color component indicated by the lesion portion or a shape of the lesion portion and include a first pixel evaluation value and a second pixel evaluation value respectively indicating a degree of first feature and a degree of second feature, relevant to the color component indicated by the lesion portion or the color component and the shape of the lesion portion, for each pixel from the image, a representative value calculation unit configured to calculate a plurality of representative evaluation values including a first representative evaluation value of the first feature and a second representative evaluation value of the second feature of the imaged biological tissue by integrating each of the plurality of pixel evaluation values of each of the pixels in the image for each of the plurality of features of the appearance, and an integration unit configured to calculate one numerical value in which at least two representative evaluation values of the plurality of representative evaluation values are calculated and integrated, as the severity of the lesion.

It is preferable that the integration unit is configured to perform different calculations in accordance with an increase or decrease in at least one representative evaluation value of the plurality of representative evaluation values, in order to calculate the one numerical value.

It is preferable that in the different calculations, a set of at least two representative evaluation values to be used in the calculation is different.

One embodiment of the present invention is an endoscope system. The endoscope system, includes:

an electronic endoscope configured to image a biological tissue in a body cavity;

a processor including an image processing unit configured to obtain a severity of a lesion of the biological tissue in which a degree of lesion is represented as one value by using information of a color component of an image of a lesion portion of the biological tissue, from the image that is obtained by the electronic endoscope; and a monitor configured to display information of the severity. The image processing unit includes a feature amount calculation unit configured to calculate two pixel evaluation values of a first pixel evaluation value and a second pixel evaluation value, which are capable of discriminating each of a first feature and a second feature of an appearance appearing in the lesion portion from a normal portion of the biological tissue by a color component indicated by the lesion portion or a shape of the lesion portion and respectively indicate a degree of first feature and a degree of second feature, relevant to the color component indicated by the lesion portion or the color component and the shape of the lesion portion, for each pixel from the image, a representative value calculation unit configured to calculate a first representative evaluation value of the first feature of the imaged biological tissue by integrating the first pixel evaluation values of each of the pixels in the image and a second representative evaluation value of the second feature of the imaged biological tissue by integrating the second pixel evaluation values of each of the pixels in the image, and an integration unit configured to calculate one numerical value in which the first representative evaluation value and the second representative evaluation value are calculated and integrated, as the severity of the lesion.

It is preferable that the degree of second feature is a degree of color component included in a portion having a predetermined shape in the image.

It is preferable that the degree of second feature is a degree of feature of a predetermined shape in a portion having the predetermined shape in the image.

It is preferable that the degree of first feature is a degree of color component indicated by the lesion portion of the image.

It is preferable that the first pixel evaluation value is a value indicating a degree of feature relevant to a color component indicating a degree of inflammation of the biological tissue, and the second pixel evaluation value is a value indicating a degree of color component included in a blood vessel region indicating a blood vessel extending into the shape of a streak in the image.

It is preferable that the color component of the image includes a red component, a green component, and a blue component, and the feature amount calculation unit is configured to calculate the first pixel evaluation value on the basis of a deviation angle deviating with respect to a reference axis set in advance, in which in a color space that is defined by the red component, the blue component, or the green component, direction of a line segment connecting a reference point set in the color space and a pixel corresponding point corresponding to the color component of each of the pixels of the image passes through the reference point.

It is preferable that the integration unit is configured to change the calculation of the severity between a case in which the first representative evaluation value or the second representative evaluation value is greater than a threshold value and a case in which the first representative evaluation value or the second representative evaluation value is not greater than the threshold value.

It is preferable that the integration unit is configured to calculate the severity by subtracting the second representative evaluation value from the first representative evaluation value in a case in which the second representative evaluation value is greater than or equal to a threshold value, and by adding the second representative evaluation value to the first representative evaluation value in a case in which the second representative evaluation value is less than the threshold value.

It is preferable that the degree of first feature is a degree of color component indicated by the lesion portion of the image, and the degree of second feature is a degree of color component included in a portion having a predetermined shape in the image.

It is preferable that the feature amount calculation unit is configured to calculate a third pixel evaluation value indicating a degree of third feature relevant to the color component indicated by the lesion portion, which is different from the first feature and the second feature, for each of the pixels, the representative value calculation unit is configured to calculate a third representative evaluation value of the third feature of the imaged biological tissue by integrating the third pixel evaluation values of each of the pixels in the image, and the integration unit is configured to calculate the severity by subtracting the second representative evaluation value from the first representative evaluation value in a case in which the second representative evaluation value is greater than or equal to a threshold value, and by adding the third representative evaluation value to the first representative evaluation value in a case in which the second representative evaluation value is less than the threshold value.

It is preferable that the first pixel evaluation value is a value indicating a degree of feature relevant to a color component indicating a degree of inflammation of the biological tissue, the second pixel evaluation value is a value indicating a degree of color component included in a blood vessel region indicating a blood vessel extending into the shape of a streak in the image, and the third pixel evaluation value is a value indicating a degree of feature relevant to a color component indicating a degree of ulcer of the biological tissue.

Advantageous Effects of Invention

According to the endoscope system described above, it is possible to accurately evaluate the degree of lesion in a lesion portion of a biological tissue.

BRIEF DESCRIPTION OF DRAWINGS

FIG. 7 is a diagram illustrating an example of a filter coefficient in the case of using a template TP1 illustrated in FIG. 6 as a space filter.

FIG. 8 is a diagram schematically illustrating a distribution range of a subjective evaluation result of a medical doctor with respect to an image of a lesion portion, on an orthogonal coordinate system of a representative value of a biological tissue reddish degree and a representative value of a blood vessel reddish degree.

FIG. 9 is a diagram illustrating an example of a flow of processing for calculating a severity of a lesion portion by a processor for an electronic endoscope of one embodiment.

DESCRIPTION OF EMBODIMENTS

Figure 1:
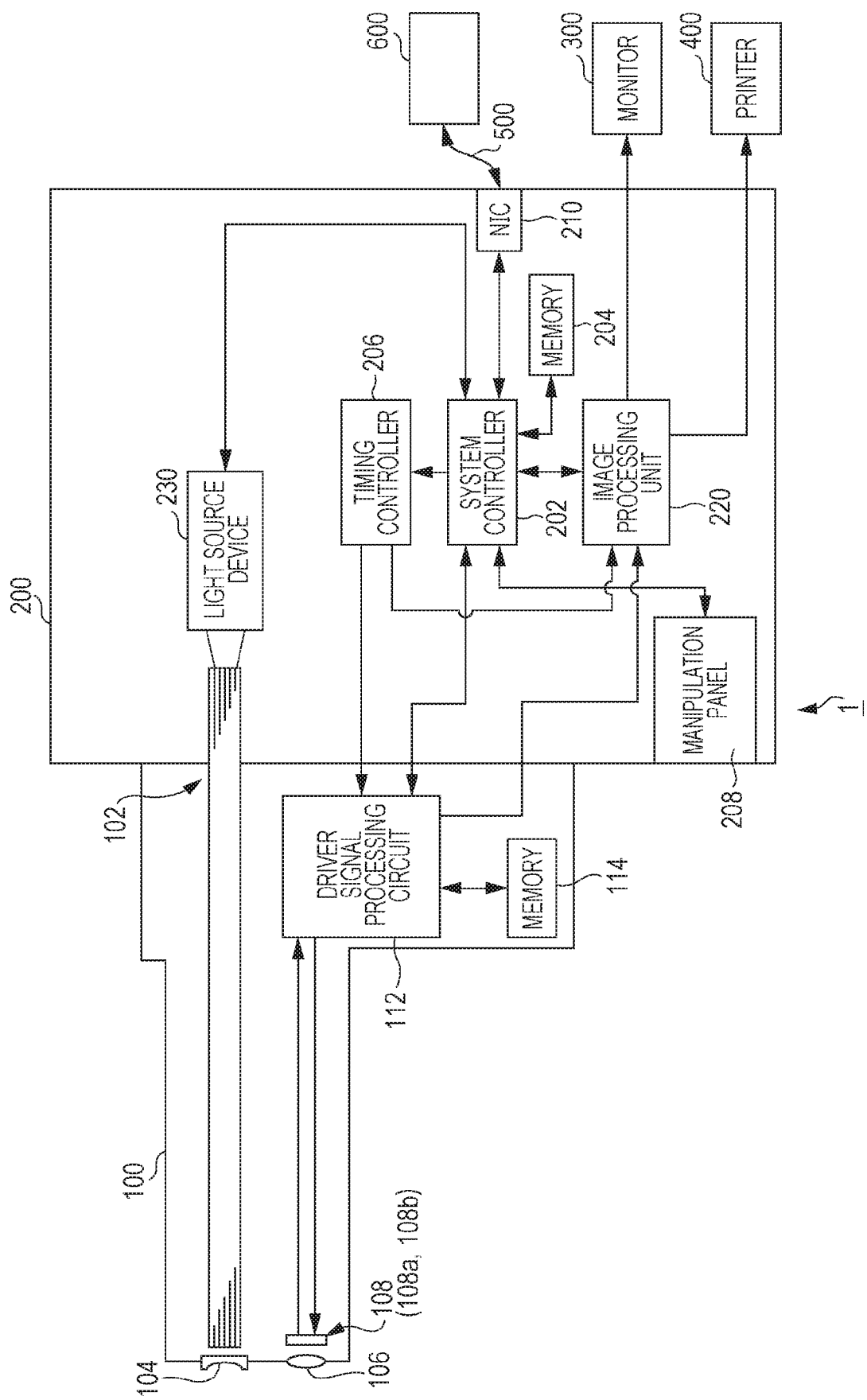
FIG. 1 is a block diagram illustrating a configuration of an endoscope system according to an embodiment.

Hereinafter, first, the concept of an endoscope system will be described, and then, an endoscope system of an embodiment of the present invention will be described with reference to the drawings.

A lesion portion in a biological tissue has various degrees of lesion of a lesion portion from an inflamed site to an ulcer site. In an endoscope system of the related art, only an inflamed site is set to an evaluation target, and the degree of inflammation of the inflamed site is evaluated on the basis of information of a color component of the inflamed site (for example, a red color). Such an evaluation result may not sufficiently correspond to evaluation of a medical doctor, including an inflammation to an ulcer, or a histological evaluation result. For this reason, an endoscope system of one embodiment calculates a plurality of pixel evaluation values corresponding to a plurality of features of an appearance appearing in a lesion portion, which are capable of discriminating each of the plurality of features of the appearance from the feature of a normal portion of a biological tissue by a color component indicated by the lesion portion or the shape of the lesion portion, for each pixel from an image of the biological tissue. Further, the endoscope system calculates a plurality of representative evaluation values by integrating the calculated pixel evaluation values of each of the pixels for each of the plurality of features of the appearance, and calculates one numerical value in which at least two representative evaluation values of the plurality of representative evaluation values are calculated and integrated, as a severity of a lesion.

As described above, the severity of the lesion of the lesion portion is calculated by using the pixel evaluation value of each of the pixels relevant to the plurality of features of the appearance, and thus, the severity of the lesion of the lesion portion can be accurately evaluated, compared to the case of performing evaluation by using only the degree of red color indicated by the biological tissue, as with the related art.

As one embodiment, in a case where the feature of the appearance is a first feature and a second feature, the degree of first feature is the degree of specific color component indicated by the lesion portion, for example, the degree of red color included in the biological tissue, and a first pixel evaluation value for each pixel in which the degree of first feature is digitized, for example, is a biological tissue reddish degree in which the degree of red color is digitized. The second feature is the degree of color component included in a portion having a specific shape in the imaged biological tissue, and a second pixel evaluation value for each pixel in which the degree of second feature is digitized, for example, is a blood vessel reddish degree in which the degree of red color included in a blood vessel region extending into the shape of a streak is digitized, in the lesion portion and the periphery thereof. In the inflamed site, when the blood vessel reddish degree is greater than or equal to a predetermined threshold value, the blood vessel reddish degree tends to decrease as the biological tissue reddish degree increases, and when the blood vessel reddish degree is less than the predetermined threshold value, the blood vessel reddish degree tends to increase as the biological tissue reddish degree increases. According to one embodiment, when the blood vessel reddish degree is greater than or equal to the predetermined threshold value, the severity is calculated by subtracting a representative value of the blood vessel reddish degree (a second representative evaluation value) from a representative value of the biological tissue reddish degree (a first representative evaluation value), and when the blood vessel reddish degree is less than the predetermined threshold value, the severity is calculated by adding the representative value of the blood vessel reddish degree to the representative value of the biological tissue reddish degree. That is, the severity is obtained by integrating the first representative evaluation value and the second representative evaluation value. The severity calculated as described above excellently corresponds to a subjective evaluation result of a medical doctor (for example, a MAYO endoscopic subscore) or a histological evaluation result.

In addition, in a case where the feature of the appearance is a first feature, a second feature, and a third feature, as an example, the degree of first feature is a specific color component indicated by the lesion portion, for example, the degree of red color, the degree of second feature is the degree of color component included in a portion having a specific shape in the imaged biological tissue, and the degree of third feature is a specific color component indicated by the lesion portion, for example, the degree of white color.

The degree of feature of the appearance includes a degree relevant to a shape, and for example, may be the degree of shape of surface asperity of the lesion portion or the degree of predetermined shape such as surface modeling.

One numerical value in which the plurality of representative evaluation values are integrated may be a calculation result in which the obtained plurality of representative evaluation values are calculated, or may be a calculation result in which some representative evaluation values of all representative evaluation values are calculated. In this case, representative evaluation values that are not used in the calculation may be used as an index for performing different calculation in accordance with an increase or decrease in the representative evaluation value.

FIG. 1 is a block diagram illustrating the configuration of an electronic endoscope system 1 of one embodiment of the present invention. As illustrated in FIG. 1, the electronic endoscope system 1 includes an electronic scope 100, a processor 200 for an electronic endoscope, a monitor 300, and a printer 400.

The processor 200 for an electronic endoscope includes a system controller 202 and a timing controller 206. The system controller 202 executes various programs stored in a memory 204, and controls integrally the entire electronic endoscope system 1. In addition, the system controller 202 changes various settings of the electronic endoscope system 1 in accordance with an instruction of a user (an operator or an assistant) that is input into a manipulation panel 208. The timing controller 206 outputs a clock pulse for adjusting a performance timing of each unit to each circuit in the electronic endoscope system 1.

The processor 200 for an electronic endoscope includes a light source unit 230 supplying illumination light to the electronic scope 100. Even though it is not illustrated, the light source unit 230, for example, includes a high-luminance lamp emitting white illumination light by receiving the supply of driving power from a lamp power source, for example, a xenon lamp, a metal halide lamp, a mercury lamp, or a halogen lamp. The light source unit 230 is configured such that the illumination light exiting from the high-luminance lamp is condensed by a light condensing lens that is not illustrated, and then, is incident on an incident end of a light carrying bundle (LCB) 102 that is a bundle of optical fibers of the electronic scope 100 through a light control device that is not illustrated.

Alternatively, the light source unit 230 includes a plurality of light emitting diodes allowing light in a wavelength band of a predetermined color to exit. The light source unit 230 is configured such that the light exiting from the light emitting diode is synthesized by using an optical element such as dichroic mirror, and the synthesized light is condensed by the light condensing lens that is not illustrated, as the illumination light, and then, is incident on the incident end of the light carrying bundle (LCB) 102 of the electronic scope 100. A laser diode can also be used instead of the light emitting diode. The light emitting diode and the laser diode have features such as low power consumption and a small heat release value, and thus, there is an advantage that it is possible to obtain a bright image while suppressing the power consumption and e heat release value, compared to other light sources. A bright image can be acquired, and thus, the accuracy of an evaluation value relevant to the lesion described below can be improved.

Note that, in the example illustrated in FIG. 1, the light source unit 230 is provided by being embedded in the processor 200 for an electronic endoscope, but may be provided in the electronic endoscope system 1, as a device separate from the processor 200 for an electronic endoscope. In addition, the light source unit 230 may be provided on the distal tip of the electronic scope 100 described below. In this case, the LCB 102 guiding the illumination light is not necessary.

The illumination light incident into the LCB 102 from the incident end propagates through the LCB 102 and exits from the exiling end of the LCB 102 that is disposed on the distal tip of the electronic scope 100, and is applied to an object through a light distribution lens 104. Reflection light from the object forms an optical image on a light receiving surface of a solid image sensor 108 through an objective lens 106.

The solid image sensor 108, for example, is a single-plate type color charge-coupled device (CCD) image sensor in which various filters such as infra red (IR) cut filter 108a and a Bayer array color filter 108b are disposed on the light receiving surface, and generates each primary color signal of red (R), green (G), and blue (B) according to the optical image formed on the light receiving surface. A single-plate type color complementary metal oxide semiconductor (CMOS) image sensor can also be used instead of the single-plate type color CCD image sensor. In general, in the CMOS image sensor, an image tends to be generally dark, compared to the CCD image sensor. Accordingly, an advantageous effect that it is possible to suppress a variation in the severity of the lesion of the lesion portion clue to the brightness of the image, in digitization processing for evaluating the lesion described below, is remarkable compared to the case of using the CMOS image sensor. As described above, the electronic scope 100 images the biological tissue in a body cavity by using the solid image sensor 108.

A driver signal processing circuit 112 is provided in a connection portion of the electronic scope 100. The driver signal processing circuit 112 generates an image signal (a luminance signal Y and a color difference signals Cb and Cr) by performing predetermined signal processing such as color interpolation and matrix calculation with respect to the primary color signal that is input by the solid image sensor 108, and outputs the generated image signal to an image processing unit 220 of the processor 200 for an electronic endoscope. In addition, the driver signal processing circuit 112 accesses a memory 114, and reads out intrinsic information of the electronic scope 100. The intrinsic information of the electronic scope 100 that is recorded in the memory 114, for example, includes the number of pixels or sensitivity, a performable frame rate, a model number, and the like of the solid image sensor 108. The driver signal processing circuit 112 outputs the intrinsic information that is read out from the memory 114 to the system controller 202.

The system controller 202 performs various calculations on the basis of the intrinsic information of the electronic scope 100, and generates a control signal. The system controller 202 controls the performance or the timing of each of the circuits in the processor 200 for an electronic endoscope by using the generated control signal such that processing suitable for the electronic scope 100 being connected to the processor 200 for an electronic endoscope is performed.

The tinting controller 206 supplies the clock pulse to the driver signal processing circuit 112, the image processing unit 220, and the light source unit 230, in accordance with timing control of the system controller 202. The driver signal processing circuit 112 drives and controls the solid image sensor 108 at a timing synchronized with a frame rate of a video that is processed on the processor 200 for an electronic endoscope side, in accordance with the clock pulse that is supplied from the timing controller 206.

The image processing unit 220 generates a video signal for displaying an endoscope image or the like on the monitor, on the basis of the image signal input by the driver signal processing circuit 112, and outputs the video signal to the monitor 300, under the control of the system controller 202. Further, the image processing unit 220 obtains the severity of the lesion in which the degree of lesion of the biological tissue is digitized by using a color component of the image or shape information, from an image of the lesion portion of the biological tissue, which is obtained by the electronic scope 100. In addition, the image processing unit 220 generates a color map image in which color replacement is performed on the basis of the biological tissue reddish degree that is obtained at the time of performing the digitization processing for obtaining the severity. The image processing unit 220 generates a video signal for displaying severity information and the color map image on the monitor, and outputs the video signal to the monitor 300. Accordingly, the operator is capable of receiving the severity of a lesion of an attention biological tissue through an image displayed on a display screen of the monitor 300. The image processing unit 220, as necessary, outputs the color map image and the severity information to the printer 400.

The processor 200 for an electronic endoscope is connected to a server 600 through a network interface card (NIC) 210 and a network 500. The processor 200 for an electronic endoscope is capable of downloading information relevant to an endoscopic examination (for example, electronic chart information of a patient or information of an operator) from the server 600. The downloaded information, for example, is displayed on the display screen of the monitor 300 or the manipulation panel 208. In addition, the processor 200 for an electronic endoscope uploads an endoscopic examination result (endoscope image data, an examination condition, an image analysis result, operator findings, and the like) to the server 600, and thus, is capable of storing the endoscopic examination result in the server 600.

Figure 2:
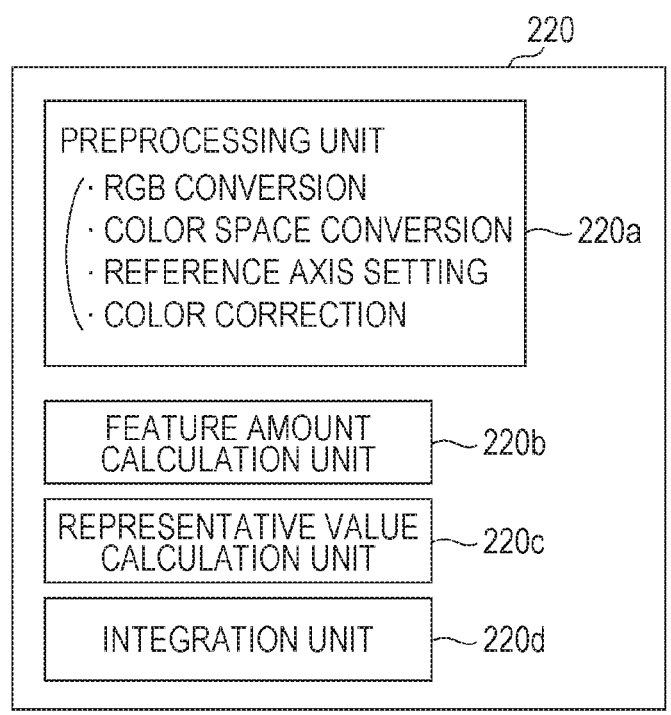
FIG. 2 is a diagram describing a configuration of an image processing unit of one embodiment, which performs digitization processing with respect to a severity of a lesion portion.

FIG. 2 is a diagram describing the configuration of the image processing unit 220 performing the digitization processing for digitizing the degree of feature of the lesion, in order to calculate the severity of the lesion of the biological tissue. The image processing unit 220 obtains the severity of the lesion that is obtained by digitizing the degree of lesion of the biological tissue, from the image of the biological tissue, which is obtained by the electronic scope 100. The image processing unit 220 includes a preprocessing unit 220*a*, a feature amount calculation unit 220*b*, a representative value calculation unit 220*c*, and an integration unit 220*d*.

As one embodiment, the feature amount calculation unit 220*b* calculates the biological tissue reddish degree in which the degree of red color of the biological tissue is digitized for each pixel, as the first pixel evaluation value, and calculates the blood vessel reddish degree in which the red color of the blood vessel region extending into the shape of a streak on the biological tissue is digitized, as the second pixel evaluation value. Hereinafter, a form of calculating the biological tissue reddish degree and the blood vessel reddish degree will be described.

The preprocessing unit 220*a* performs preprocessing with respect to an image for evaluating the degree of red color indicated by the biological tissue. As illustrated an example, the preprocessing unit 220*a* performs each processing of RGB conversion, color space conversion, reference axis setting, and color correction.

The preprocessing unit 220*a* converts the image signal that is input by the driver signal processing circuit 112 (the luminance signal Y and the color difference signals Cb and Cr) into an image color component (R, G, and B) by using a predetermined matrix coefficient.

Further, the preprocessing unit 220*a* performs color space conversion for orthogonally projecting image data that is converted into the image color component onto an RG plane. Specifically, image color components of each pixel of an RGB color space that is defined by three primary colors of RGB are converted into image color components of RG. Conceptually, the image color components of each of the pixels of the RGB color space are plotted in the RG plane (for example, a section in the RG plane in which Pixel Value of R Component=0 to 255 and Pixel Value of G Component=0 to 255 are obtained), in accordance with the pixel values of the R and G components. Hereinafter, for the convenience of description, points of the image color components of each of the pixels of the RGB color space and points of the image color components that are plotted in the RG color space will be referred to as a "pixel corresponding point". The image color components of each of RGB of the RGB color space, for example, are sequentially a color component having a wavelength of 620 nm to 750 nm, a color component having a wavelength of 495 nm to 570 nm, and a color component having a wavelength of 450 nm to 495 nm. Note that, the color components configure the color space (also including the color plane). A color phase and a chromaticness are excluded from the "color component".

In the preprocessing unit 220*a*, a reference axis in the RG plane that is necessary for evaluating the biological tissue reddish degree and the blood vessel reddish degree is set.

In the biological tissue of the body cavity of the patient, which is the object, the R component of the image color components is dominant over the other components (the G component and the B component) by the influence of a hemoglobin pigment or the like. In a case where the degree of lesion of the lesion portion is low, and the lesion portion is the inflamed site, the red color (the R component) is intensified with respect to other colors (the G component and the B component) as the inflammation becomes severe. However, the color of the image obtained by imaging the body cavity is changed in accordance with a photographing condition affecting the brightness (for example, an exposing condition of the illumination light). Illustratively, a shaded portion that is not exposed to the illumination light is black (an achromatic color, for example, the values of the image color component of R, G, and B are zero or a value close to zero), and a portion that is strongly exposed to the illumination light and is subjected to normal reflection is white (an achromatic color, for example, the values of the image color components of R, G, and B are 255 or a value close to 255 in the case of an 8-bit shade). That is, even in the case of imaging the same inflamed site in which the inflammation occurs, a pixel value of the inflamed site increases as being strongly exposed to the illumination light. For this reason, the value of the color component of the image may have no correlation with the severeness of the inflammation, in accordance with the exposing condition of the illumination light.

In general, a normal site in the body cavity in which the inflammation does not occur is covered with a sufficient mucosal membrane. In contrast, the inflamed site in the body cavity in which the inflammation occurs is not covered with a sufficient mucosal membrane. Specifically, the blood vessel expands and the blood and the body fluid are leaked out from the blood vessel, and thus, the mucosal membrane becomes relatively thin, and the color of the blood is likely to be visible. The mucosal membrane basically has a white tone, but is slightly yellow as a color, and the color (the yellow color) on the image is changed in accordance with a contrasting density of the mucosal membrane (the thickness of the mucosal membrane). Accordingly, it is considered that the contrasting density of the mucosal membrane is also one of the indices for evaluating the degree of inflammation.

Figure 3:
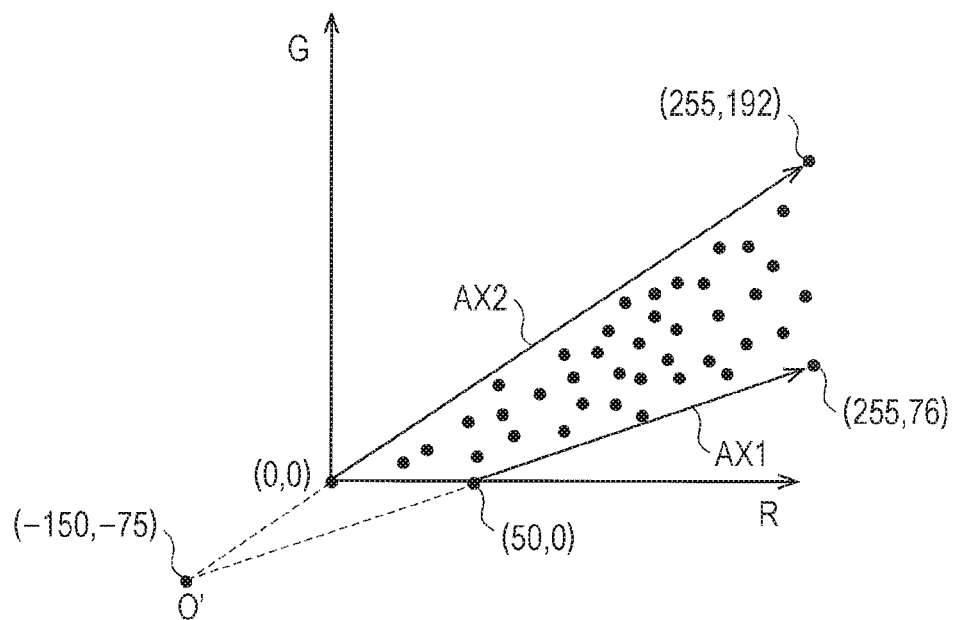
FIG. 3 is a diagram describing an example of a reference axis in a color space, which is used in one embodiment.

Therefore, as illustrated in FIG. 3, in the RG color space, a straight line passing through (50,0) and (255,76) is set as one of the reference axes, and a straight line passing through (0,0) and (255,192) is set as one of the reference axes. For the convenience of description, the reference axis of the former will be referred to as a "hemoglobin change axis AX1", and the reference axis of the latter will be referred to as a "mucosal membrane change axis AX2". FIG. 3 is a diagram describing an example of the reference axis in the color space, which is used in one embodiment.

Plots illustrated in FIG. 3 are obtained as the result of analyzing a plurality of reference images in the body cavity. The reference image used in the analysis includes an inflammation image example at each degree such as an inflammation image example in which the degree of inflammation is highest (an inflammation image example of the most severe level) or an inflammation image example in which the degree of inflammation is lowest (an image example that is substantially regarded as the normal site). Note that, in the example illustrated in FIG. 3, for the convenience of clarifying the drawings, only a part of the plots that are obtained as the result of the analysis is illustrated. The number of plots that are actually obtained as the result of the analysis is considerably greater than the number of plots illustrated in FIG. 3.

As described above, the R component of the color components of the image is intensified with respect to the other components (the G component and the B component) as the inflammation becomes severe. For this reason, an axis on a boundary line between a region in which the plots are distributed and a region in which the plots are not distributed, which is closer to an R axis than a G axis, in the example illustrated in FIG. 3, an axis on a boundary line passing through (50,0) and (255,76) is set as an axis having a high correlation with a portion in which the degree of inflammation is most intensified, that is, a site in which the degree of inflammation is highest. The axis is the hemoglobin change axis AX1. A plot corresponding to an inflamed site in which the degree of inflammation is highest, imaged in various photographing conditions, for example, the exposing condition of the illumination light, is superimposed on the hemoglobin change axis AX1. Therefore, the hemoglobin change axis AX1 is an axis on which the pixel corresponding points to be plotted converge as the degree of inflammation of the biological tissue increases.

On the other hand, the G component (or the B component) of the color components of the image is intensified with respect to the R component as being close to the normal site. For this reason, an axis on the boundary line between the region in which the plots are distributed and the region in which the plots are not distributed, which is closer to the G axis than the R axis, in the example illustrated in FIG. 3, an axis on a boundary line passing through (0,0) and (255,192) is set as an axis having a high correlation with a portion in which the degree of inflammation is lowest, that is, a portion that is substantially regarded as the normal site. The axis is the mucosal membrane change axis AX2. A plot corresponding to the portion in which the degree of inflammation is lowest, that is, the portion that is substantially regarded as a normal portion, imaged in various photographing conditions, for example the exposing condition of the illumination light, is superimposed on the mucosal membrane change axis AX2. Therefore, the mucosal membrane change axis AX2 is an axis on which the pixel corresponding points to be plotted converge as the degree of inflammation decreases (as being close to the normal site).

For supplement, the portion in which the degree of lesion of the lesion portion is highest is accompanied by bleeding. On the other hand, the portion in which the degree of lesion is lowest is the normal site that is substantially normal, and thus, is covered with a sufficient mucosal membrane. For this reason, it is possible to grasp that the plots in the RG color space, illustrated in FIG. 3, are distributed in a region between an axis having the highest correlation with the color of the blood (the hemoglobin pigment) and an axis having the highest correlation with the color of the mucosal membrane. For this reason, in the boundary line between the region in which the plots are distributed and the region in which the plots are not distributed, the boundary line close to the R axis (the R component is intensified) corresponds to an axis indicating the inflamed site in which the degree of inflammation is highest (the hemoglobin change axis AX1), and the boundary line close to the G axis (the G component is intensified) corresponds to an axis indicating the inflamed site in which the degree of inflammation is lowest (the mucosal membrane change axis AX2).

The reference axis is set as described above, and then, processing for calculating the biological tissue reddish degree indicating the degree of red color, described below, is performed with respect to the color component of the image that is orthogonally projected. Color correction is performed with respect to the pixel data that is orthogonally projected, before the processing for calculating the biological tissue reddish degree.

The reference axis illustrated in FIG. 3 is an example, and the reference axis is different in accordance with the type of illness.

The preprocessing unit 220a performs the color correction with respect to the color component of the image represented by the RG color space, before the calculation of an inflammation evaluation value. A correction matrix coefficient is stored in a memory which is not illustrated. The preprocessing unit 220a performs correction with respect to the pixel data (R and G) that is the pixel corresponding point in the RG color space of each of the pixels, as indicated in the following expression by using the correction matrix coefficient, such that the inflammation evaluation value described below does not vary at the time of imaging the same inflamed site with different electronic endoscope systems (in other words, such that an error between electronic scopes is suppressed).

$$\begin{pmatrix} R_{new} \\ G_{new} \end{pmatrix} = \begin{pmatrix} M_{00} & M_{01} \\ M_{10} & M_{11} \end{pmatrix} \begin{pmatrix} R \\ G \end{pmatrix}$$

$R_{new}$: Pixel Data after Correction (R Component)
$G_{new}$: Pixel Data after Correction (G Component)
$M_{00}$ to $M_{11}$: Correction Matrix Coefficient
R: Pixel Data before Correction (R Component)
G: Pixel Data before Correction (G Component)

Figure 4:
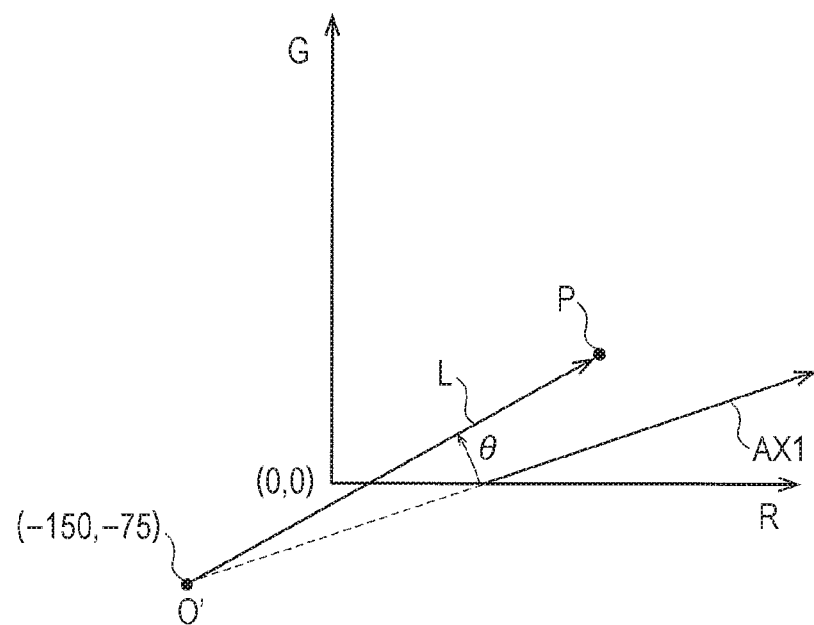
FIG. 4 is a diagram describing a method for calculating a deviation angle for calculating the degree of inflammation, which is used in one embodiment.

The feature amount calculation unit 220b selects one attention pixel from the pixels, and calculates a deviation angle for calculating the biological tissue reddish degree, the degree of inflammation, on the basis of information of a color component of the attention pixel, with respect to the selected attention pixel. That is, the digitization processing for digitizing the degree of red color of the biological tissue is performed on the basis of the information of the color component of the pixel. FIG. 4 is a diagram describing a method for calculating the deviation angle for calculating the biological tissue reddish degree, which is used in one embodiment. Specifically, as illustrated in FIG. 4, the feature amount calculation unit 220b sets an intersection point between the hemoglobin change axis AX1 and the mucosal membrane change axis AX2 to a reference point O', and calculates a deviation angle θ at which the direction of a line segment L connecting the reference point O' and a pixel corresponding point P of the attention pixel deviates with respect to the reference axis AX1. Note that, the reference point O' is positioned at coordinates (−150,−75). An example in which the reference point O' is at the coordinates (−150,−75) is described, but the present invention is not limited thereto. The reference point O' can be suitably changed, and for example, may be an intersection point between the R axis and the G axis in the RG color space.

A preferred coordinate position as the reference point O', for example, is a position in which an error in evaluation results due to a variation in the brightness can be reduced. Specifically, it is preferable to set the reference point O' by obtaining in advance a point at which an error between an evaluation result in a dark portion (a luminance is less than a predetermined value) and an evaluation result in a non-dark portion (the luminance is greater than or equal to the predetermined value) is minimized.

In addition, for example, in a case where the reference point O' is set between coordinates (−10,−10) and coordinates (10,10), a change amount of the angle θ in a case where the pixel corresponding point is changed increases, compared to a case where the coordinates (−150,−75) or the like are set as the reference point O', and thus, resolution is improved. Accordingly, it is possible to obtain an evaluation result having a high accuracy.

On the other hand, the reference point O' is set between coordinates (−50,−50) and coordinates (−200,−200), and thus, an evaluation result indicating the degree of inflammation is hardly affected by a noise.

In a case where the brightness of the image obtained by photographing the biological tissue in the body cavity is changed in accordance with an exposing condition of white light, the color of the image is affected by an individual difference, a photographing spot, the state of the inflammation, and the like, and in the RG color space, in general, the color of the image is changed along the hemoglobin change axis AX1 in the inflamed site in Which the severity is highest, and is changed along the mucosal membrane change axis AX2 in the inflamed site in which the degree of inflammation is lowest. In addition, it is assumed that the color of the image in the inflamed site in which the degree of inflammation is intermediate is changed with the same tendency. That is, in a case where there is a change according to the exposing condition of the illumination light, the pixel corresponding point corresponding to the inflamed site is shifted in an azimuthal direction originating from the reference point O'. In other words, in a case where there is a change according to the exposing condition of the illumination light, the pixel corresponding point corresponding to the inflamed site is moved at a constant deviation angle θ with respect to the mucosal membrane change axis AX2, and thus, a distance with respect to the reference point O' is changed. This indicates that the deviation angle θ is a parameter that is not substantially affected by a change in the brightness of the image.

The R component is intensified with respect to the G component as the deviation angle θ is small, which indicates that the degree of red color in the lesion portion is relatively high. In addition, the G component is intensified with respect to the R component as the deviation angle θ is large, which indicates that the degree of red color is relatively low. Therefore, the feature amount calculation unit 220b normalizes the angle θ such that the value is 255 when the deviation angle θ is zero, and the value is zero when the deviation angle θ is $θ_{MAX}$. Note that, $θ_{MAX}$ is identical to an angle between the hemoglobin change axis AX1 and the mucosal membrane change axis AX2. That is, the feature amount calculation unit 220b performs the digitization processing for digitizing the degree of red color on the basis of the information of the color component of each attention pixel, with respect to each of the attention pixels, and thus, obtains the biological tissue reddish degree (the first pixel evaluation value) falling within a range of 0 to 255.

Note that, the attention pixel is selected with respect to all the pixels of the image one by one.

Note that, in the example illustrated in FIG. 4, the RG color space is used as the color space, but an RB color space can also be used instead of the RG color space.

The feature amount calculation unit 220b calculates the biological tissue reddish degree as the first pixel evaluation value, on the basis of the deviation angle θ, and in some cases, calculates a biological tissue whiteness degree (a third pixel evaluation value) indicating the degree of feature of an ulcer of the biological tissue, described below. For example, gain adjustment for applying a linear gain is performed with respect to the pixel value of each of the color components of each of the pixels of the image of the biological tissue, a dynamic range in the vicinity of a color gamut specific to the lesion is substantially widened, and tone emphasis processing for increasing effective resolution of color representation is performed, and thus, for example, an ulcer site of an ulcerative colitis that includes tongue fur or mucopus exhibits a white color, and can be discriminated from the inflamed site that includes edema and easy bleeding properties and exhibits a red color or the normal site that exhibits a yellow color or a green color, by the color component. The biological tissue whiteness degree can be calculated by using a deviation angle with respect to a reference axis different from the hemoglobin change axis AX1, which is represented on a color space having a coordinate axis of two color components as illustrated in FIG. 4 (two of the R component, the G component, and the B component) or three color components (the R component, the G component, and the B component). Note that, the tone emphasis processing is performed by the preprocessing unit 220a.

Further, the feature amount calculation unit 220b prepares the color map image in which the image of the biological tissue is formed into a mosaic by a display color that is changed in accordance with the biological tissue reddish degree. In order to enable the color map image to be displayed, a table in which the pixel evaluation value and a predetermined display color are associated with each other is stored in a storage region of a memory or the like which is not illustrated. In the table, for example, a different display color is associated at five-value intervals. Illustratively, in a case where the pixel evaluation value is in a range of 0 to 5, a blue color is associated, a different display color is associated in accordance with an arrangement sequence of colors in a color circle each time when the pixel evaluation value increases by 5, and in a case where the pixel evaluation value is in a range of 250 to 255, a red color is associated. The display color, for example, is a color that becomes closer to a warm color from a cold color such that the color is changed to a yellow color and a red color from a blue color as the biological tissue reddish degree is high. The feature amount calculation unit 220b determines the display color of the selected attention pixel on the color map image in accordance with the biological tissue reddish degree of the attention pixel, with reference to the table.

As described above, the feature amount calculation unit 220*b* prepares the color map image to which a color is applied in accordance with the biological tissue reddish degree.

Further, the feature amount calculation unit 220*b* determines the certainty of the blood vessel region of the biological tissue in the image that is obtained by imaging the biological tissue, on the basis of a shape featuring the blood vessel, and as necessary, extracts the blood vessel region by the obtained certainty.

Figure 5:
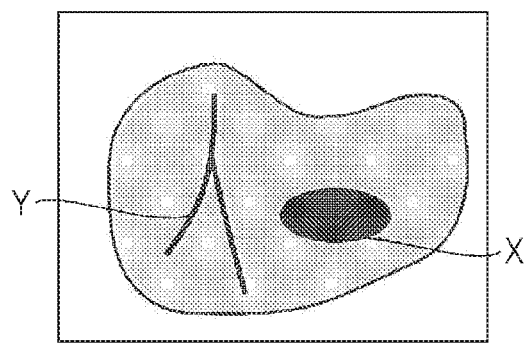
FIGS. 5(a) and 5(b) are diagrams schematically describing an example of an image of a biological tissue and an example of a color map image that is obtained by a method of the related art.
Figure 5:
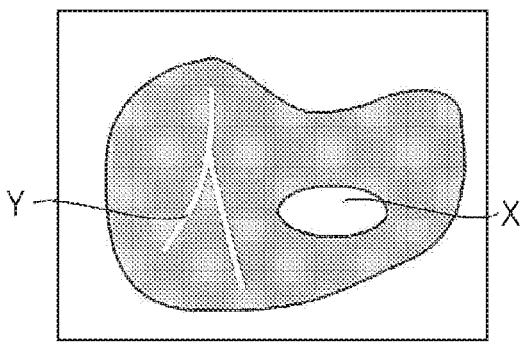

As illustrated in FIG. 5(*a*), the image obtained by imaging the biological tissue includes an image of a blood vessel region Y in the shape of a streak, which is visible through the mucosal membrane, in the vicinity of a lesion portion X. In a color map image illustrated in FIG. 5(*b*) in which such an image is color-coded in accordance with the biological tissue reddish degree described above, the blood vessel region Y may be displayed by the same color as that of the inflamed site. FIGS. 5(*a*) and 5(*b*) are diagrams schematically describing an example of the image of the biological tissue and an example of a color map image that is obtained by a method of the related art.

The feature amount calculation unit 220*b* obtains the certainty of the blood vessel region Y, and extracts the blood vessel region Y on the basis of the certainty.

Figure 6:
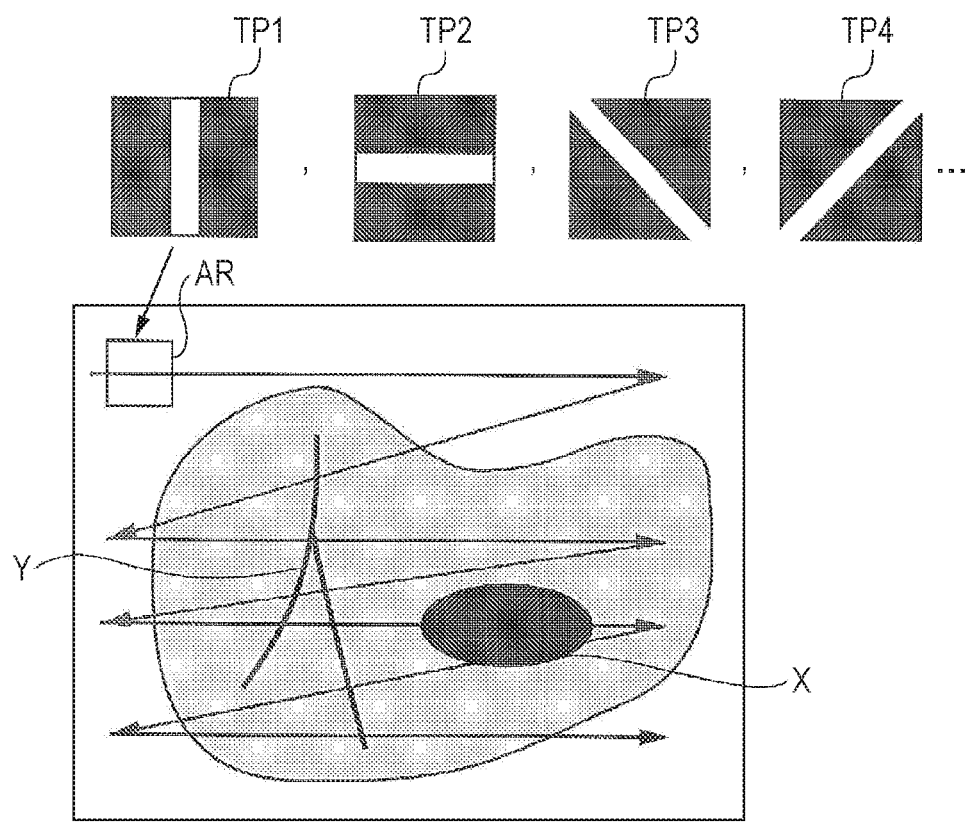
FIG. 6 is a diagram describing an example of a method for extracting a blood vessel region in one embodiment.

FIG. 6 is a diagram describing an e of a method for extracting the blood vessel region Y in one embodiment.

The feature amount calculation unit 220*b* obtains a matching degree representing the degree of correlation between the shape of a part of an examination target area. AR in the image of the biological tissue and each linear shape of a plurality of templates TP1 to TP4, and sets the highest matching degree in the matching degrees respectively corresponding to the plurality of templates TP1 to TP4 as the certainty of the blood vessel region Y in the examination target area AR. The templates TP1 to TP4 are configured of pixels, and the templates TP1 to TP4 have a plurality of linear shapes in which extension directions of straight lines are different from each other. In the templates TP1 to TP4, each pixel has a pixel value in conformance to each of the linear shapes. As illustrated in FIG. 6, the examination target area AR is moved while being sequentially overlapped along an arrow from the end of the image, and thus, a correlation degree between the pixel evaluation value of the image in the examination target area AR and the value of the pixel corresponding to each of the templates TP1 to TP4 is obtained. According to one embodiment, the templates TP1 to TP4 have four linear shapes in which the straight lines extend in four different extension directions, as the shape featuring the blood vessel. In a case where the examination target area AR includes the blood vessel region, the pixel value in the examination target area AR includes information of a feature shape in which the blood vessel extends into the shape of a streak, and thus, the blood vessel region Y can be extracted by using an image having the pixel evaluation value that is set in accordance with the deviation angle θ, as the pixel value. The templates TP1 to TP4 have a value for each pixel corresponding to a white region and a black region illustrated in FIG. 6. For this reason, according to one embodiment, the matching degree is a correlation coefficient between the value of the pixel of the templates TP1 to TP4 and the pixel evaluation value corresponding to the examination target region AR. In addition, according to one embodiment, the matching degree may be a value in which the values of each of the pixels of the templates TP1 to TP4 are set as a filter coefficient of a space filter, and each of the filter coefficients and an image evaluation value of the pixel corresponding to the examination target area AR are multiplied and added up.

The highest matching degree in the matching degrees calculated with respect to each of the templates TP1 to TP4 is set as a value indicating the certainty of the blood vessel region, and is applied to the center pixel of the examination target area AR.

FIG. 7 is a diagram illustrating an example of the filter coefficient in a case where the template TP1 is used as the space filter. As illustrated in FIG. 6, the template TP1 has a shape in which the straight line extends in an up-and-down direction in the drawing. In FIG. 7, as an example, the template TP1 configures a space filter of 5×5 pixels. In this case, ⅕ is applied to pixels of a portion that extends linearly, as the filter coefficient, and −1/20 is applied to the other pixels, as the filter coefficient. When a value in which each filter coefficient and the same image evaluation value of the pixel corresponding to the examination target area AR are multiplied and added up is calculated as the matching degree, the matching degree becomes zero in a case where all of the pixel evaluation values of the examination target area AR are the same value. On the other hand, in a case where the image of the blood vessel extending into the shape of a streak in up-and-down direction is included in the examination target area AR, the matching degree increases. It can be described that an image close to the template TP1 is included as the value of the matching degree is large. Therefore, the matching degree is calculated with respect to each of the templates TP1 to TP4, and the highest matching degree in the calculated matching degrees is set as the certainty of the blood vessel region Y and is applied to the center pixel of the examination target region AR. That is, the value of the certainty of the blood vessel region Y is applied to the center pixel of the examination target area AR.

Such a matching degree is a result of performing space filtering with respect to the pixel evaluation value that is the biological tissue reddish degree, by using each of the templates TP1 to TP4, and thus, the value of each pixel of an image in which each of the pixels has the pixel evaluation value that is processed by the space filtering includes information of a matching degree at the time of matching to any of the templates TP1 to TP4, and the image obtained by the space filtering has a pixel value reflecting the blood vessel region Y. Therefore, the feature amount calculation unit 220*b* determines whether or not the value of the certainty of the blood vessel in each of the pixels is greater than a value set in advance, and in a case where the value of the certainty of the blood vessel in the pixel is greater than the value set in advance, the feature amount calculation unit 220*b* determines that the pixel is in the blood vessel region Y, and thus, extracts the blood vessel region Y.

The feature amount calculation unit 220*b* sets the biological tissue reddish degree in the pixel corresponding to the extracted blood vessel region Y as the blood vessel reddish degree. In this case, the blood vessel reddish degree in a region not corresponding to the blood vessel region Y is zero. In addition, the feature amount calculation unit 220*b* may obtain a value in which the certainty of the blood vessel is normalized in a range of 0 to 1, and may obtains a result of correcting the biological tissue reddish degree such that the biological tissue reddish degree increases as the value increases and the biological tissue reddish degree decreases as the value decreases, as the blood vessel reddish degree. As described above, the blood vessel reddish degree is calculated with respect to all the pixels. For example, a result of multiplying the value of the biological tissue reddish degree by the value of the certainty of the blood vessel may be obtained as the blood vessel reddish degree.

As described above, the feature amount calculation unit 220b of one embodiment calculates the biological tissue reddish degree as the first pixel evaluation value, and calculates the blood vessel reddish degree as the second pixel evaluation value. Therefore, the first pixel evaluation value in the embodiment is an evaluation value indicating the degree of color co orient indicated by the inflamed site of the image, and the second pixel evaluation value is an evaluation value indicating the degree of color component included in a portion having the shape of the blood vessel in the image.

The representative value calculation unit 220c calculates the representative value of the biological tissue reddish degree (the first representative evaluation value) of the biological tissue that is imaged by integrating the biological tissue reddish degrees (the first pixel evaluation values) of each of the pixels that are calculated by the feature amount calculation unit 220b, and calculates the representative value of the blood vessel reddish degree (the second representative evaluation value) that is imaged by integrating the blood vessel reddish degrees (the second pixel evaluation value) of each of the pixels that are calculated by the feature amount calculation unit 220b.

Processing for integrating the biological tissue reddish degree and the blood vessel reddish degree in each of the pixels may be averaging processing for calculating the biological tissue reddish degree and the blood vessel reddish degree of each of the pixels, or may be another known processing such as processing for obtaining, for example, a median value. The averaging processing includes processing for obtaining a simple average value and processing for obtaining a weighted average value. In addition, the known processing may be processing for calculating a representative value by dividing each of the biological tissue reddish degree and the blood vessel reddish degree into at least two or more levels that are ranked and by assigning an addition value P of a value in which the number of pixels belonging to each of the levels is multiplied by a predetermined weighting coefficient to a predetermined expression. In this case, the predetermined expression, for example, is $1/(1+e^{-P})$. In this case, it is preferable that the weighting coefficient is a coefficient that is obtained by multiple logistic regression analysis to have a correlation with the subjective evaluation result of the medical doctor.

The integration unit 220d calculates the severity of the lesion by integrating the representative value of the biological tissue reddish degree (the first representative evaluation value) and the representative value of the blood vessel reddish degree (the second representative evaluation value). The representative value of the biological tissue reddish degree (the first representative evaluation value) and the representative value of the blood vessel reddish degree (the second representative evaluation value) are integrated by calculation such as addition and subtraction between the representative value of the biological tissue reddish degree and the representative value of the blood vessel reddish degree. For example, when the representative value of the blood vessel reddish degree is greater than or equal to a predetermined threshold value, a result of subtracting the representative value of the blood vessel reddish degree from the representative value of the biological tissue reddish degree is set to the severity, and when the representative value of the blood vessel reddish degree is less than the predetermined threshold value, a result of adding the representative value of the biological tissue reddish degree and the representative value of the blood vessel reddish degree is set to the severity.

The integration unit 220d generates a signal for displaying the calculated severity on the screen along with the color map image prepared by the feature amount calculation unit 220b, and sends the signal to the monitor 300.

FIG. 8 is a diagram schematically illustrating a distribution range of a MAYO endoscopic subscore that is the subjective evaluation result of the medical doctor with respect to 100 images of the lesion portion of the ulcerative colitis. In FIG. 8, the distribution range of the MAYO endoscopic subscore is illustrated on an orthogonal coordinate system of the representative value of the biological tissue reddish degree and the representative value of the blood vessel reddish degree. Each of MAYO 0, MAYO 1, and MAYO 2 in the drawing represents that the MAYO endoscopic subscore is 0, 1, and 2. It is indicated that the severity of the lesion increases from MAYO 0 to MAYO 2.

As can be seen from FIG. 8, in general, it is illustrated that the biological tissue reddish degree increases while the blood vessel reddish degree decreases, from MAYO 0 to MAYO 1. In addition, in general, it is illustrated that both of the blood vessel reddish degree and the biological tissue reddish degree increase, from MAYO 1 to MAYO 2. Therefore, from such a fact, it is found that it is preferable to change the method for calculating the severity in accordance with whether representative value of the blood vessel reddish degree is greater than or equal to a predetermined threshold value TH or less than the predetermined threshold value TH, from the viewpoint of corresponding to the MAYO endoscopic subscore.

The processor 200 for an electronic endoscope including the image processing unit 220 calculates the severity of the lesion along a flow illustrated in FIG. 9, and displays the severity on the monitor 300. FIG. 9 is a diagram illustrating an example of a flow of processing for calculating the severity of the lesion by the processor 200 for an electronic endoscope of one embodiment.

First, the image processing unit 220 acquires an image of the current frame (step S10).

Next, the preprocessing unit 220a performs the preprocessing including the RGB conversion, the color space conversion, the reference axis setting, and the color correction, and as necessary, the tone emphasis processing, described above, and the feature amount calculation unit 220b calculates the plurality of pixel evaluation values indicating the degree of each of the plurality of features of the color component indicated by the lesion portion or the shape (the first pixel evaluation value, the second pixel evaluation value, and the third pixel evaluation value), for example, the biological tissue reddish degree, the blood vessel reddish degree, the biological tissue whiteness degree, and the like, with respect to the image subjected to the preprocessing, for each of the pixels (step S12).

The feature amount calculation unit 220b determines whether or not to calculate the pixel evaluation value with respect to all the pixels of the image of the current frame (step S14). In a case where the calculation of the pixel evaluation value all the pixels is completed, the representative value calculation unit 220c calculates the representative value in which the pixel evaluation values are integrated (the first representative evaluation value, the second representative evaluation value, or the third representative evaluation value) (step S16). The representative value is calculated for each type of pixel evaluation value.

After that, the integration unit 220d calculates one severity by combining a plurality of representative values (step S18). That is, one numerical value in which the plurality of representative values are calculated and integrated is calculated as the severity of the lesion. Note that, in the combination of the plurality of representative values, a combining method (an integrating method) of the representative value most excellently corresponding to the subjective evaluation result in the plurality of representative values in the image of the biological tissue in which the subjective evaluation result of the medical doctor can be obtained is established by regression analysis or the like.

Figure 10:
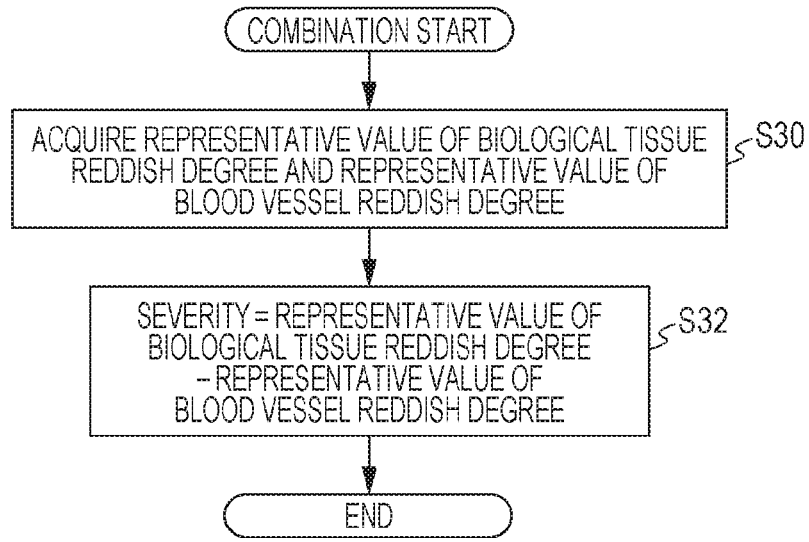
FIG. 10 is a diagram illustrating an example of a flow of a combination of representative values for integration, which is used in one embodiment.

FIG. 10 is a diagram illustrating an example of a flow of the combination of the representative values, which is used in one embodiment. In the example illustrated in FIG. 10, the biological tissue reddish degree and the blood vessel reddish degree are used as the first pixel evaluation value and the second pixel evaluation value. The integration unit 220d acquires the representative value of the biological tissue reddish degree and the representative value of the blood vessel reddish degree that are calculated by the representative value calculation unit 220c (step S30). The integration unit 220d subtracts the representative value of the blood vessel reddish degree from the representative value of the biological tissue reddish degree, and sets the subtraction result to the severity (step S32). Note that, in the subtraction, a value obtained by multiplying the representative value of the blood vessel reddish degree by a constant β may be subtracted from a value obtained by multiplying the representative value of the biological tissue reddish degree by a constant α.

Such a severity accurately corresponds to the subjective evaluation result of the medical doctor, in the inflamed site (in FIG. 8, MAYO 0 to MAYO 1). As illustrated in FIG. 8, a distribution is illustrated in which the representative value of the biological tissue reddish degree increases and the representative value of the blood vessel reddish degree decreases, as the degree of inflammation of the inflamed site is high. Therefore, even in a case where the representative values of the biological tissue reddish degree are incidentally the same, it is possible to determine an increase or decrease in the severity by a difference in the representative values of the blood vessel reddish degree. Similarly, even in a case where the representative values of the blood vessel reddish degree are incidentally the same, it is possible to determine an increase or decrease in the severity by a difference in the representative values of the biological tissue reddish degree.

Figure 11:
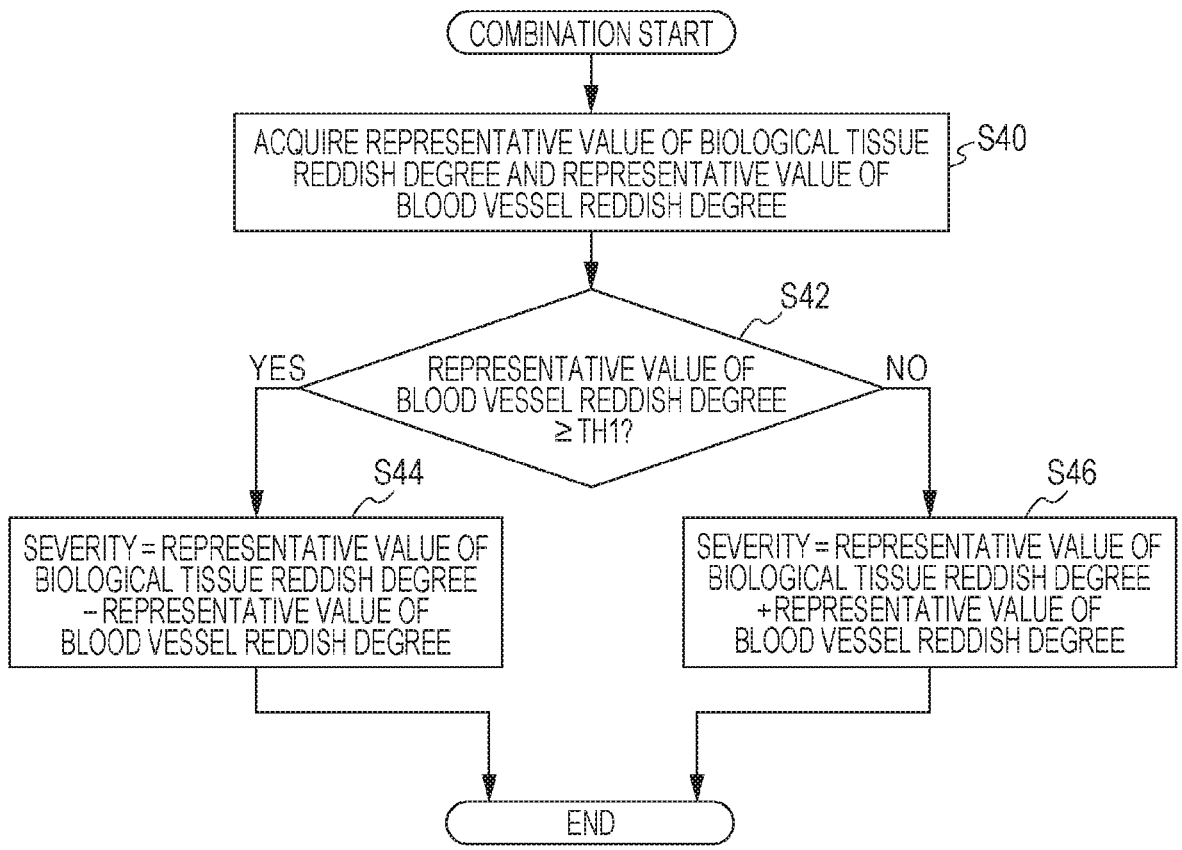
FIG. 11 is a diagram illustrating an example of a flow of a combination of representative values for integration, which is different from the flow illustrated in FIG. 10 and is used in one embodiment.

FIG. 11 is a diagram illustrating an example of a flow of the combination of the representative values, which is different from the flow illustrated in FIG. 10 and is used in one embodiment. In the example illustrated in FIG. 11, the biological tissue reddish degree and the blood vessel reddish degree are used as the first pixel evaluation value and the second pixel evaluation value. The integration unit 220d acquires the representative value of the biological tissue reddish degree and the representative value of the blood vessel reddish degree that are calculated by the representative value calculation unit 220c (step S40). The integration unit 220d determines whether or not the representative value of the blood vessel reddish degree is greater than or equal to a threshold value TH1 set in advance (step S42). In a case where the representative value of the blood vessel reddish degree is greater than or equal to the threshold value TH1 set in advance, the integration unit 220d subtracts the representative value of the blood vessel reddish degree from the representative value of the biological tissue reddish degree, and sets the subtraction result to the severity (step S44). Note that, in the subtraction, a value obtained by multiplying the representative value of the blood vessel reddish degree by a constant β may be subtracted from a value obtained by multiplying the representative value of the biological tissue reddish degree by a constant α.

On the other hand, in a case where the representative value of the blood vessel reddish degree is less than the threshold value TH1 set in advance, the integration unit 220d adds the representative value of the biological tissue reddish degree and the representative value of the blood vessel reddish degree, and sets the addition result to the severity (step S46). Note that, in the addition, the value obtained by multiplying the representative value of the biological tissue reddish degree by the constant α and the value obtained by multiplying the representative value of the blood vessel reddish degree by the constant β may be added.

As described above, the reason that the calculation of the severity is changed in accordance with whether the representative value of the blood vessel reddish degree is greater than or equal to the threshold value TH1 or less than the threshold value TH1 is because, as illustrated in FIG. 8, in a case where the representative value of the blood vessel reddish degree is high, a movement as with an arrow A illustrated in FIG. 8 is obtained as the severity increases (MAYO 0→MAYO 1), and in a case where the representative value of the blood vessel reddish degree is low, a movement as with an arrow B illustrated in FIG. 8 is obtained as the severity increases (MAYO 1 MAYO 2). For this reason, the calculation of the severity is changed by using the threshold value TH1 as a boundary. Therefore, it is possible to accurately determine an increase or decrease in the severity of the lesion of the lesion portion including the inflamed site (MAYO 0→MAYO 1) and the ulcer site (MAYO 1→MAYO→2). Note that, the representative value of the biological tissue reddish degree may be compared with the threshold value TH2 (refer to FIG. 8) instead of comparing the representative value of the blood vessel reddish degree with the threshold value TH1, and the calculation of the severity may be changed in accordance with the comparison result, as with step S44 and step S46.

Returning to FIG. 9, the integration unit 220d generates a signal for displaying the color map image to be generated from the pixel evaluation value calculated in step S12 and the severity calculated in step S18 on the screen, and sends the signal to the monitor 300. Accordingly, the monitor 300 displays the color map image and the severity information (step S20).

As described above, the image processing unit 220 repeats the processing while the photographed image is sequentially sent from the electronic scope 100 (step S22).

As described above, in the color component indicated by the biological tissue, the image processing unit 220 calculates the pixel evaluation values (the first pixel evaluation value and the second pixel evaluation value) indicating the degree of each of the plurality of features in the lesion, for each of the pixels from the image, calculates the representative evaluation Values (the first representative evaluation value and the second representative evaluation value) of a feature amount corresponding to the plurality of features by integrating each of the plurality of pixel evaluation values, and calculates one numerical value in which the plurality of representative evaluation values are integrated by calculation, as the severity of the lesion of the lesion portion in the biological tissue. For this reason, the severity of the lesion is calculated by using the plurality of pixel evaluation values, and thus, it is possible to accurately evaluate the severity of the lesion in the lesion portion, compared to the case of performing evaluation by using only the information of the red color of the biological tissue, as with the related art.

Figure 12:
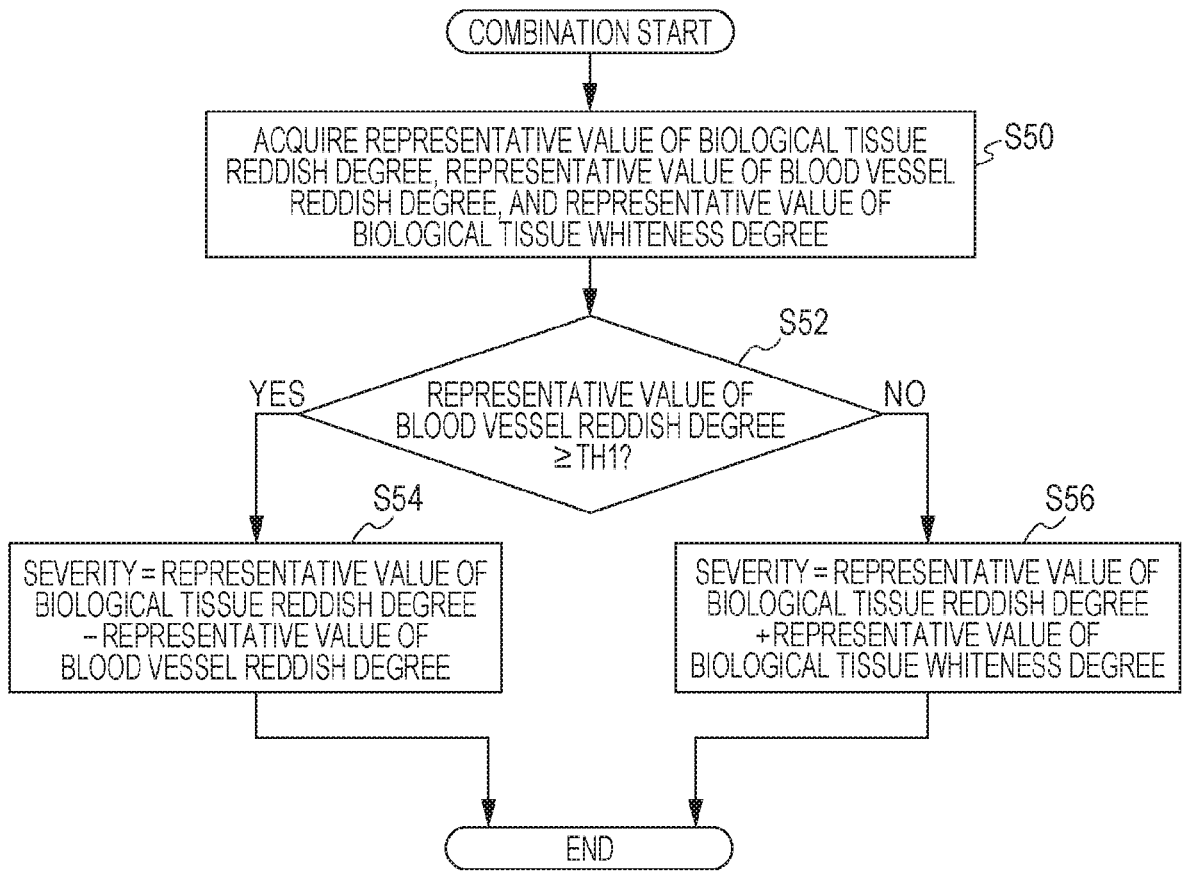
FIG. 12 is a diagram illustrating an example a flow of one embodiment for calculating a severity by using three pixel evaluation values.

In both examples of the combination of the representative values of the pixel evaluation values, illustrated in FIGS. 10 and 11, the severity is calculated by using the biological tissue reddish degree and the blood vessel reddish degree, as two pixel evaluation values, and the severity cats be calculated by using three or more pixel evaluation values. FIG. 12 is a diagram illustrating an example a flow of one embodiment for calculating the severity by using three pixel evaluation values.

In the example illustrated in FIG. 12, the biological tissue reddish degree, the blood vessel reddish degree, and the biological tissue whiteness degree are used as three pixel evaluation values. The biological tissue whiteness degree indicates the degree of feature of the ulcer in the biological tissue. For example, gain adjustment for applying a non-linear gain is performed with respect to the pixel value of each of the color components of each of the pixels of the image of the biological tissue, the dynamic range in the vicinity of the color gamut specific to the lesion is substantially widened, and the tone emphasis processing for increasing the effective resolution of the color representation is performed, and therefore, for example, the ulcer site in the ulcerative colitis includes tongue fur or mucopus, and thus, exhibits a white color. On the other hand, the inflamed site that includes edema or easy bleeding properties exhibits a red color, and the normal site exhibits a yellow color or a green color. Therefore, the biological tissue whiteness degree is calculated by using the deviation angle with respect to the reference axis different from the reference axis such as the hemoglobin change axis AX1 illustrated in FIG. 4, which is represented on the color space having the coordinate axis of two color components as illustrated in FIG. 4 (two of the R component, the G component, and the B component) or three color components (the R component, the G component, and the B component). Such a biological tissue whiteness degree is calculated by the feature amount calculation unit 220b along with the biological tissue reddish degree and the blood vessel reddish degree, and the representative value of the biological tissue whiteness degree is calculated by the representative value calculation unit 220c along with a biological tissue red color portion and a blood vessel red color portion. As described above, the integration unit 220d acquires the representative value of the biological tissue red color portion, the representative value of the blood vessel reddish degree, and the representative value of the biological tissue whiteness degree, which are calculated by the representative value calculation unit 220c (step S50).

The integration unit 220d determines whether or not the representative value of the blood vessel reddish degree is greater than or equal to the threshold value TH1 set in advance (step S52). In a case where the representative value of the blood vessel reddish degree is greater than or equal to the threshold value TH1 set in advance, the integration unit 220d subtracts the representative value of the blood vessel reddish degree from the representative value of the biological tissue reddish degree, and sets the subtraction result to the severity (step S54). Note that, in the subtraction, a value obtained by multiplying the representative value of the blood vessel reddish degree by a constant may be subtracted from a value obtained by multiplying the representative value of the biological tissue reddish degree by a constant $\alpha$.

On the other hand, in a case where the representative value of the blood vessel reddish degree is less than the threshold value TH1 set in advance, the integration unit 220d adds the representative value of the biological tissue reddish degree and the representative value of the biological tissue whiteness degree, and sets the addition result to the severity (step S56). Note that, in the addition, a value obtained by multiplying the representative value of the biological tissue reddish degree by the constant $\alpha$ and a value obtained by multiplying the representative value of the biological tissue whiteness degree by the constant $\beta$ may be added.

The representative value of the biological tissue whiteness degree is identical to the color component indicated by the tongue fur or the mucopus of the ulcer site, and indicates the degree of white color, and thus, the representative value of the biological tissue whiteness degree increases as the degree of lesion increases. In addition, in a case where the degree of lesion increases, the blood vessel is hardly visible (the red color of the blood vessel becomes inconspicuous), and thus, when the degree of lesion is severe, the representative value of the blood vessel reddish degree is small. For this reason, the threshold value TH1 of the blood vessel reddish degree is used as a boundary between the case of including only the inflamed site and the case of including the inflamed site and the ulcer site. As described above, it is possible to simultaneously evaluate the degree of inflammation and the degree of ulcer in the biological tissue, and thus, the evaluation result accurately corresponds to the subjective evaluation result of the medical doctor.

In the example illustrated in FIG. 12, in step S52, it is determined whether or not the representative value of the blood vessel reddish degree is greater than the threshold value TH1 set in advance, and the severity is calculated by performing the calculation of step S54 or step S56, in accordance with the determination result, and thus, the severity may be discontinuously changed at the representative value of the blood vessel reddish degree in the vicinity of the threshold value TH1, In such a case, the severity may be obtained as a result in which the representative value of the blood vessel reddish degree is subtracted from the representative value of the biological tissue reddish degree, and the representative value of the biological tissue whiteness degree is added, without performing step S52 for determining whether or not the representative value of the blood vessel reddish degree is greater than or equal to the threshold value TH1 set in advance. That is, the integration unit 220d may be configured to calculate one numerical value in which three representative evaluation values that are acquired are calculated and integrated, as the severity of the lesion. In this case, when the representative value of the blood vessel reddish degree is subtracted from the representative value of the biological tissue reddish degree, a value obtained by multiplying the representative value of the blood vessel reddish degree by a constant may be subtracted from the representative value of the biological tissue reddish degree, and when the representative value of the biological tissue whiteness degree is added, a value obtained by multiplying the representative value of the biological tissue whiteness degree by a constant may be added.

Figure 13:
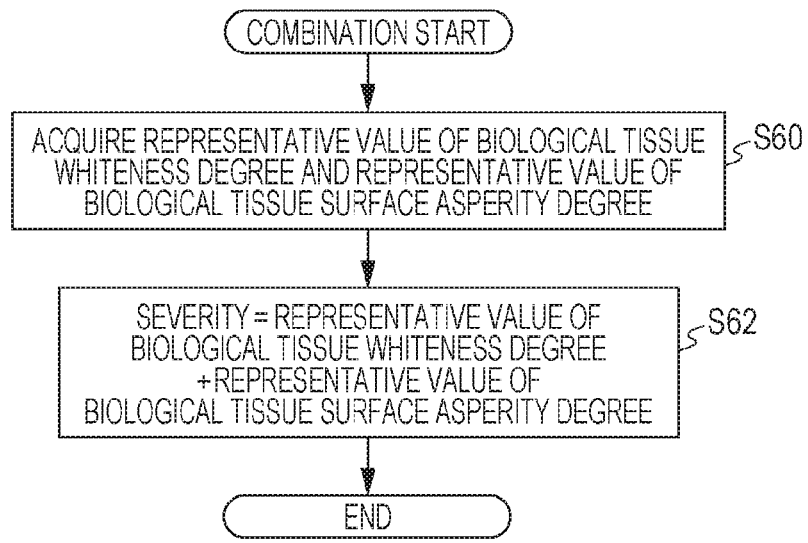
FIG. 13 is a diagram illustrating an example of a flow of a combination of one embodiment, which is different from a combination of representative values of the pixel evaluation values illustrated in FIG. 12.

In the embodiment described above, the pixel evaluation value indicating the degree of feature relevant to the color component indicated by the lesion portion, such as the biological tissue reddish degree, the blood vessel reddish degree, and the biological tissue whiteness degree, are calculated, and a pixel evaluation value indicating the degree of feature relevant to the shape of the lesion portion can be calculated, and the severity of the lesion can also be calculated by using a representative value of the pixel evaluation value. FIG. 13 is a diagram illustrating an example of a flow of a combination of one embodiment, which is different from the combination of the representative values of the pixel evaluation values illustrated in FIG. 12.

In a Crohn disease different from the ulcerative colitis, a lesion portion includes an ulcer site, and a biological tissue surface has a concave and convex shape, and thus, the Crohn disease has different features in the ulcerative colitis and the biological tissue surface. For this reason, in order to evaluate the degree of lesion of the lesion portion of the Crohn disease, a pixel evaluation value indicating the degree of feature relevant to the shape of the lesion portion is calculated. The degree of feature relevant to the shape, for example, is the degree of asperity of the biological tissue surface.

In a case where the degree of feature relevant to the shape is the degree of asperity of the biological tissue surface, the degree of asperity can be evaluated by edge intensity that can be obtained by using a known edge detection filter in an image of a luminance component (a Y signal). Therefore, the feature amount calculation unit 220b calculates a biological tissue surface asperity degree for each pixel, on the basis of the edge intensity that is obtained by using an edge detection filter. The value of the biological tissue surface asperity degree increases as the asperity of the biological tissue surface increases.

As described above, the feature amount calculation unit 220b calculates the biological tissue whiteness degree indicating the degree of feature of the ulcer of the biological tissue.

The representative value calculation unit 220c obtains representative values of the biological tissue whiteness degree and the biological tissue surface asperity degree. The representative value of the biological tissue surface asperity degree is not particularly limited, as with the representative value of the biological tissue reddish degree, the blood vessel reddish degree, or the like, and may be an average value or a median value, or may be a value that is calculated from known processing.

As illustrated in FIG. 13, the integration unit 220d acquires a representative value of a biological tissue white color portion and the representative value of the biological tissue surface asperity degree (step S60).

The integration unit 220d adds the representative value of the biological tissue white color portion and the representative value of the biological tissue surface asperity degree, which are acquired, and sets the addition result to the severity (step S62). In the addition, a value obtained by multiplying the representative value of the biological tissue whiteness degree by the constant β and a value obtained by multiplying the representative value of the biological tissue surface asperity degree by a constant γ may be added.

As described above, the representative value of the biological tissue whiteness degree and the representative value of the biological tissue surface asperity degree are added, and the addition result is set to the severity, and thus, in the Crohn disease in which the lesion is often accompanied by the ulcer, the surface asperity increases as the lesion progresses, and therefore, even in a case where the color components of the ulcer are incidentally the same, it is possible to determine an increase or decrease in the severity by a difference in the biological tissue surface asperity degrees. In addition, even in a case where the degrees of surface asperity are incidentally the same, it is possible to determine an increase or decrease in the severity by a difference in the biological tissue whiteness degrees indicating the degree of color component of the ulcer of the biological tissue.

As described above, the image processing unit 220 calculates the pixel evaluation value indicating the degree of feature relevant to the color component indicated by the lesion portion or the color component and the degree of feature relevant to the shape, for each of the pixels from the image, calculates the representative evaluation value of the feature amount corresponding to the plurality of features by integrating the pixel evaluation values for each type of pixel evaluation value, and calculates one numerical value in which the plurality of representative evaluation values are calculated and integrated, as the severity of the lesion. For this reason, it is possible to accurately evaluate the degree of lesion in the lesion portion, compared to the case of performing evaluation by using only the information of the red color of the biological tissue, as with the related art.

Note that, the degree of feature relevant to the shape may be the shape of surface modeling indicating a texture shape, in addition to the concave and convex shape of the surface. In the degree of surface modeling, a co-occurrence matrix is prepared by using a known filter in the image of the luminance component (the Y signal), and thus, each pixel can be evaluated.

Note that, the degree of one feature (the second feature) in the color component indicated by the lesion portion is the degree of color component included in a portion having a predetermined shape in the image, for example, the portion of the blood vessel in the shape of a streak, for example, the degree of red color. For this reason, the degree of red color of the blood vessel region is evaluated in addition to the degree of red color of the biological tissue, and thus, it is possible to accurately evaluate the degree of lesion of the inflamed site in an inflammatory bowel disease, compared to the related art.

The degree of one feature (the second feature) indicated by the lesion portion is a predetermined shape in the image, for example, the biological tissue the degree of surface asperity or the degree of surface modeling. For this reason, it is possible to accurately evaluate the degree of lesion of the Crohn disease or the like, on the basis of the degree of ulcer and the degree of predetermined shape such as the asperity degree of the biological tissue surface.

One of the pixel evaluation values is a color component indicating the degree of inflammation of the biological tissue, for example, a value indicating the degree of feature relevant to a red color, for example, the biological tissue reddish degree, and one of the pixel evaluation values is a color component of the blood vessel region indicating the blood vessel extending into the shape of a streak in the image, for example, a value indicating the degree of red color included in the blood vessel region, for example, the blood vessel reddish degree. For this reason, it is possible to accurately evaluate the degree of lesion of the inflamed site in the inflammatory bowel disease, compared to the related art.

The color component of the photographed image that is sent from the electronic scope 100 includes the red component, the green component, and the blue component, and as illustrated in FIG. 4, in the color space that is defined by the red component, the blue component, or the green component, the feature amount calculation unit 220b calculates the pixel evaluation value on the basis of the deviation angle θ at which the direction of the line segment L connecting the reference point O' set in the color space and the pixel corresponding point P corresponding to the color component of each pixel of the image deviates with respect to the reference axis such as the hemoglobin change axis AX1, and thus, in the inflammatory bowel disease, it is possible to objectively evaluate the inflammation regardless of whether the image is bright or dark.

In addition, as illustrated in FIG. 8, the calculation of the severity is different between a case where the representative value of the biological tissue reddish degree (the first representative evaluation value) or the representative value of the blood vessel reddish degree (the second representative evaluation value) is greater than a threshold value and a case where representative value of the biological tissue reddish degree or the representative value of the blood vessel reddish degree is not greater than the threshold value, as illustrated in FIG. 11, and thus, it is possible to more accurately evaluate the degree of lesion in the lesion portion, compared to the related art. Therefore, it is preferable that the integration unit 220d is configured to perform different calculations in accordance with an increase or decrease in at least one representative evaluation value of the plurality of representative evaluation values in order to calculate one integrated numerical value.

According to one embodiment, the feature amount calculation unit 220b calculates a biological tissue surface asperity degree (a third pixel evaluation value) indicating the degree of asperity (a third feature amount) of the biological tissue surface, which is different from the degree of red color (a first feature amount) of the biological tissue relevant to the color component indicated by the lesion portion and the degree of red color (a second feature amount) of the blood vessel, for each pixel, and the integration unit 220d subtracts the representative value of the blood vessel reddish degree (the second representative evaluation value) from the representative value of the biological tissue reddish degree (the first representative evaluation value) in a case where the representative value of the blood vessel reddish degree (the second representative evaluation value) is greater than or equal to a threshold value, and adds the representative value of the biological tissue whiteness degree (the third representative evaluation value) to the representative value of the biological tissue reddish degree (the first representative evaluation value) in a case where the representative value of the blood vessel reddish degree (the second representative evaluation value) is less than the threshold value, and thus, calculates the severity. For this reason, it is possible to accurately evaluate the degree of lesion in the Crohn disease. Therefore, it is preferable that the integration unit 220d is configured to perform different calculations in accordance with an increase or decrease in at least one representative evaluation value of the plurality of representative evaluation values, in order to calculate one integrated numerical value, and at this time, in the different calculations, it is preferable that a set of at least two representative evaluation values to be used in the calculation is different as with a set of the representative value of the biological tissue reddish degree (the first representative evaluation value) and the representative value of the blood vessel reddish degree (the second representative evaluation value) and a set of the representative value of the biological tissue reddish degree (the first representative evaluation value) and the representative value of the biological tissue whiteness degree (the third representative evaluation value).

As described above, it is preferable that one of the pixel evaluation values is a value indicating the degree of feature relevant to the color component indicating the degree of ulcer of the biological tissue, for example, the biological tissue whiteness degree.

As described above, the endoscope system of the present invention has been described in detail, but the endoscope system of the present invention is not limited to the embodiment described above, and it is obvious that various improvements or modifications may be made within a range not departing from the gist of the present invention.

REFERENCE SIGNS LIST

1 Electronic endoscope system
100 Electronic scope
200 Processor for electronic endoscope
220 Image processing unit
220a Preprocessing unit
220b Feature amount calculation unit
220c Representative value calculation unit
220d Integration unit
222 Memory
224 Image memory
230 Light source unit
300 Monitor
400 Printer
600 Server

The invention claimed is:

1. An endoscope system, comprising:
an electronic endoscope configured to image a biological tissue in a body cavity;
a processor including an image processor configured to obtain a severity of a lesion of the biological tissue in which a degree of lesion is represented as one value by using at least information of a color component of an image of a lesion portion of the biological tissue, from the image that is obtained by the electronic endoscope; and
a monitor configured to display information of the severity,
wherein the image processor includes
a feature amount calculator configured to calculate a plurality of pixel evaluation values corresponding to a plurality of features of an appearance, including at least a first feature and a second feature of an appearance appearing in the lesion portion, which are capable of discriminating each of the plurality of features of the appearance from a feature of a normal portion of the biological tissue by a color component indicated by the lesion portion or a shape of the lesion portion and include a first pixel evaluation value and a second pixel evaluation value respectively indicating a degree of first feature and a degree of second feature, relevant to the color component indicated by the lesion portion or the color component and the shape of the lesion portion, for each pixel from the image,
a representative value calculator configured to calculate a plurality of representative evaluation values including a first representative evaluation value of the first feature and a second representative evaluation value of the second feature of the imaged biological tissue by integrating each of the plurality of pixel evaluation values of each of the pixels in the image for each of the plurality of features of the appearance, and
an integrator configured to calculate one numerical value in which at least two representative evaluation values of the plurality of representative evaluation values are calculated and integrated, as the severity of the lesion, wherein
the color component of the image includes a red component, a green component, and a blue component, and the feature amount calculator is configured to calculate the first pixel evaluation value based on a pixel corresponding point corresponding to the color component of each of the pixels of the image in a color space that is defined by the red component, the blue component, or the green component, as well as to calculate the second pixel evaluation value based on the shape of the lesion portion.

2. The endoscope system according to claim 1, wherein the integrator is configured to perform different calculations in accordance with an increase or decrease in at least one representative evaluation value of the plurality of representative evaluation values, in order to calculate the one numerical value.

3. The endoscope system according to claim 2, wherein in the different calculations, a set of at least two representative evaluation values to be used in the calculation is different.

4. An endoscope system, comprising:
an electronic endoscope configured to image a biological tissue in a body cavity;
a processor including an image processor configured to obtain a severity of a lesion of the biological tissue in which a degree of lesion is represented as one value by using information of a color component of an image of a lesion portion of the biological tissue, from the image that is obtained by the electronic endoscope; and
a monitor configured to display information of the severity,
wherein the image processor includes
a feature amount calculator configured to calculate two pixel evaluation values of a first pixel evaluation value and a second pixel evaluation value, which are capable of discriminating each of a first feature and a second feature of an appearance appearing in the lesion portion from a normal portion of the biological tissue by a color component indicated by the lesion portion or a shape of the lesion portion and respectively indicate a degree of first feature and a degree of second feature, relevant to the color component indicated by the lesion portion or the color component and the shape of the lesion portion, for each pixel from the image,
a representative value calculator configured to calculate a first representative evaluation value of the first feature of the imaged biological tissue by integrating the first pixel evaluation values of each of the pixels in the image and a second representative evaluation value of the second feature of the imaged biological tissue by integrating the second pixel evaluation values of each of the pixels in the image, and
an integrator configured to calculate one numerical value in which the first representative evaluation value and the second representative evaluation value are calculated and integrated, as the severity of the lesion, wherein
the color component of the image includes a red component, a green component, and a blue component, and
the feature amount calculator is configured to calculate the first pixel evaluation value based on a pixel corresponding point corresponding to the color component of each of the pixels of the image in a color space that is defined by the red component, the blue component, or the green component, as well as to calculate the second pixel evaluation value based on the shape of the lesion portion.

5. The endoscope system according to claim 1, wherein the degree of second feature is a degree of color component included in a portion having a predetermined shape in the image.

6. The endoscope system according to claim 1, wherein the degree of second feature is a degree of feature of a predetermined shape in a portion having the predetermined shape in the image.

7. The endoscope system according to claim 1, wherein the degree of first feature is a degree of color component indicated by the lesion portion of the image.

8. The endoscope system according to claim 1, wherein the first pixel evaluation value is a value indicating a degree of feature relevant to a color component indicating a degree of inflammation of the biological tissue, and
the second pixel evaluation value is a value indicating a degree of color component included in a blood vessel region indicating a blood vessel extending into the shape of a streak in the image.

9. The endoscope system according to claim 1, the feature amount calculator is configured to calculate the first pixel evaluation value on the basis of a deviation angle deviating with respect to a reference axis set in advance, in which in a color space that is defined by the red component, the blue component, or the green component, a direction of a line segment connecting a reference point set in the color space and the pixel corresponding point corresponding to the color component of each of the pixels of the image passes through the reference point.

10. The endoscope system according to claim 1, wherein the integrator is configured to change the calculation of the severity between a case in which the first representative evaluation value or the second representative evaluation value is greater than a threshold value and a case in which the first representative evaluation value or the second representative evaluation value is not greater than the threshold value.

11. The endoscope system according to claim 1, wherein the integrator is configured to calculate the severity by subtracting the second representative evaluation value from the first representative evaluation value in a case in which the second representative evaluation value is greater than or equal to a threshold value, and by adding the second representative evaluation value to the first representative evaluation value in a case in which the second representative evaluation value is less than the threshold value.

12. The endoscope system according to claim 1, wherein the degree of first feature is a degree of color component indicated by the lesion portion of the image, and
the degree of second feature is a degree of color component included in a portion having a predetermined shape in the image.

13. The endoscope system according to claim 1, wherein the feature amount calculator is configured to calculate a third pixel evaluation value indicating a degree of third feature relevant to the color component indicated by the lesion portion, which is different from the first feature and the second feature, for each of the pixels,
the representative value calculator is configured to calculate a third representative evaluation value of the third feature of the imaged biological tissue by integrating the third pixel evaluation values of each of the pixels in the image, and the integrator is configured to calculate the severity by subtracting the second representative evaluation value from the first representative evaluation value in a case in which the second representative evaluation value is greater than or equal to a threshold value, and by adding the third representative evaluation value to the first representative evaluation value in a case in which the second representative evaluation value is less than the threshold value.

14. The endoscope system according to claim 13,
wherein the first pixel evaluation value is a value indicating a degree of feature relevant to a color component indicating a degree of inflammation of the biological tissue,
the second pixel evaluation value is a value indicating a degree of color component included in a blood vessel region indicating a blood vessel extending into the shape of a streak in the image, and
the third pixel evaluation value is a value indicating a degree of feature relevant to a color component indicating a degree of ulcer of the biological tissue.

* * * * *